(12) United States Patent
Payan

(10) Patent No.: US 6,855,495 B1
(45) Date of Patent: Feb. 15, 2005

(54) TOSO AS A TARGET FOR DRUG SCREENING

(75) Inventor: Donald Payan, Hillsborough, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 499 days.

(21) Appl. No.: 09/651,150

(22) Filed: Aug. 30, 2000

Related U.S. Application Data

(63) Continuation of application No. 09/050,861, filed on Mar. 30, 1998, now Pat. No. 6,555,314.

(51) Int. Cl.[7] .......................... C12Q 1/68; G01N 33/53; C07H 21/02
(52) U.S. Cl. .................. 435/6; 435/7.21; 435/69.1; 435/70.1; 536/23.1; 536/24.3
(58) Field of Search .................. 435/6, 7.21, 7.24, 435/69.1, 70.1, 7.1; 536/23.1, 23.5, 24.3, 25.32; 436/504, 800

(56) References Cited

U.S. PATENT DOCUMENTS

| | | | |
|---|---|---|---|
| 5,512,435 A | | 4/1996 | Renschler et al. .............. 435/6 |
| 6,114,515 A | | 9/2000 | Wu et al. |
| 6,555,314 B1 | * | 4/2003 | Payan ........................... 435/6 |
| 2002/0177565 A1 | * | 11/2002 | Nolan et al. .................. 514/44 |

FOREIGN PATENT DOCUMENTS

| | | |
|---|---|---|
| EP | 0 905 238 | 3/1999 |
| WO | 99/25832 | 5/1999 |

OTHER PUBLICATIONS

Hitoshi et al., "Toso, a Cell–Surface Specific Regulator of Fas–Induced Apoptosis in T Cells," U.S. Appl. No. 60/066,063, filed Nov. 17, 1997.

Hitoshi et al., "Toso, a Cell–Surface Specific Regulator of Fas–Induced Apoptosis in T Cells," Immunity, 8:461–471 (1998).

Rothenburg et al., "Intracellular Combinatorial Chemistry with Peptides in Selection of Caspase–Like Inhibitors," Nato Advanced Science Institutes, Series H: Cell Biology, H105:171–183 (1998).

Hitoshi, Y. et al., "Retroviral Approach to Isolate Molecules that Regulate–FAS–Induced Apoptosis in T cells," Meeting Abstract. CSH Laboratory meeting, Sep. 1997. Programmed Cell Death segment.

* cited by examiner

*Primary Examiner*—Brenda Brumback
*Assistant Examiner*—Jegatheesan Seharaseyon
(74) *Attorney, Agent, or Firm*—James S. Keddie; James J. Diehl; Carol L. Francis

(57) ABSTRACT

The present invention is directed to methods for identifying novel compositions which modulate the activity of Toso, and the use of such compositions in diagnosis and treatment of disease.

3 Claims, 10 Drawing Sheets aaggagtaagcagcgtgtctccatcccctctctaggggctcttgg ATGGACCTTGCACTCTAGAAGGGACAATGGACT
TCTGGGCTTTGGCCACTTACTTCCTGCCAGTATCAGGGCCCTG AGGATCCTCCCAGAAGTAAAGGTAGAGGGGAGCTG
GGCGGATCAGTTACCATCAAATGCCCACTTCCTGAAATGCATGTGAGGATATATCTGTGCCGGGAGATGGCTGGATCTGG
AACATGTGGTACCGTGGTATCCACCACCACCAACTTCATCAAGGCAGAGTACTCTGAAGCAATACCCAC
GCAAGAATCTGTTCCTAGTGGAGTAACACAGCTGACAGAAAGTGACAGCGGAGTCTATGCCTGCGGAGCGGGCATGAAC
ACAGACCGGGAAAGACCCAGAAGTCACCCTGAAATGTCCACAGTGAATACGAGCCATCATGGGAAGAGCAGCCAATGCC
TGAGACTCCAAAATGGTTTCATCTGCCCTATTTGTTCCAGATGCCTGCATATGCCAGTTCTTCCAAATTCGTAACCAGAG
TTACCACACCAGCTCAAAGGGGCAAGGTCCCTCCAGTTCACCACTCCTCCCCCACCACCCAAATCACCCACCGCCCTCGA
GTGTCCAGAGCATCTTCAGTAGCAGGTGACAAGCCCCGAACCTTCCTGCCATCCACTACAGCCTCAAAAATCTCAGCTCT
GGAGGGGCTGCTCAAGCCCCCAGCGCCCAGCTACAACCACCACACCAGGCTGCACAGGCAGAGAGCACTGGACTATGGCT
CACAGTCTGGGAGGGAAAGGCCAAGGA TTTCACATCCTGATCCCGACCATCCTGGGCCTTTCCTGCTGGCACTTCTGGGG
CTGGTGGTGAAAAGGGCCGTTGAAAGGAGG AAAGCCCTCTCCAGGCGGGCCCGCGACTGGCCGTGAGGATGCGCGCCCT
GGAGAGCTCCCAGAGGCCCCGCGGGGTCGCGCGACCGGCTCCCAAAACAACATCTACAGCGCCTGCCCGCGGCGCGCTC
GTGGAGCGGACGCTGCAGGCACAGGGGAGGCCCCCGTTCCCGGAGCGCCGTTGCCCCCCGCCGTGCCAGGTG
TCTGAATCTCCCTGCTCCATGCCCATCTCTGAAGACCAGCTGTGAATACGTGAGCCTCTACCACCAGCCTGCCGCCAT
GATGGAGGACAGTGATTCAGATGACTACATCAATGTTCCTGCCTGA caactccccagctatccccaacccaggctcgg
actgtggtgccaaggagtctcatctatctgctgatgtccaatacctgcttcatgtgttctcagagccctcatcacttccc
atgcccatctcgactcctccatcccatctatctgtgcctgagcatggctctgcccccagtgctcttgcacaccttgc
agccccctgtagttgacaggtaagctgtagcagcaattgtcccaatgccacttgcttccttccaagccgtcg
aacagactgtgggattttgcagagtgttcttccatgtctttgaccacaggggttgttgctgcccaggctctagatcacatg
gcatcaggctggggcagaggcatagctattgtctcgggcatcctcccaggggttggtcttacacacaaatagaaggctctt
gctctgagttatgtgacgtgcctcagcccccatgactaagcaggggtctgtataaaaacactcctgaaacgcctttgc
cctgatccaaatgttagcacttgctagtgaacgtctacttatctcaagttctatgctaaaggcaattatctgatgtga
tgataaccaaacttattagcaagatatgcataatatccataaattctctttactctgtctccatccttt

FIG._1

Cording region: Capitalized
Leader sequence: Underlined
Transmembrane region: Double underlined

```
1   MDFWLWPLYF LPVSGALRIL PEVKVEGELG GSVTIKCPLP EMHVRIYLCR
51  EMAGSGTCGT VVSTTNFIKA EYKGRVTLKQ YPRKNLFLVE VTQLTESDSG
101 VYACGAGMNT DRGKTQKVTL NVHSEYEPSW EEQPMPETPK WFHLPYLFQM
151 PAYASSSKFV TRVTTPAQRG KVPPVHHSSP TTQITHRPRV SRASSVAGDK
201 PRTFLPSTTA SKISALEGLL KPQTPSYNHH TRLHRQRALD YGSQSGREGQ
251 GFHILIPTIL GLFLLALLGL VVKRAVERRK ALSRRARRLA VRMRALESSQ
301 RPRGSPRPRS QNNIYSACPR RARGADAAGT GEAPVPGPGA PLPPAPLQVS
351 ESPWLHAPSL KTSCEYVSLY HQPAAMMEDS DSDDYINVPA
```

FIG._2a

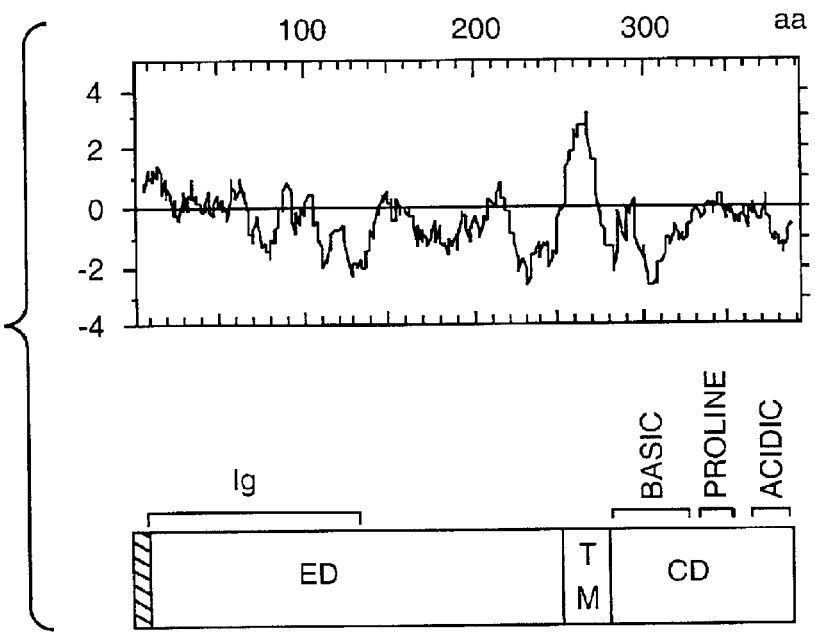

FIG._2b

```
Toso:         33  VTIKCPLPEMHV----RIMLCREMAGSSTCGTVVSTTNFIKAE-----VKGRVTLKQYPR--KNLFLVEVTQLTESDSGVYACG
IgVH:         18  LSITCTVSGSTF--SNDYMTWVRQPP-GRGLEWIGYVFYHGTSDDTTPLRSRVTMLVDTS--KNQFSLRLSSVTAADTAVYYCA
IgVλ:         37  VTLTCRSSTGAV-TTSNYANWVQQKPDHLFTGGGTNNRAPGVP-----ARFSGSLIG----NKAALTITGAQTEDEAIYFCA
TcR Vα:       39  TSLNCTFSDSA----SQYFMWYRQHSGKAPKALMSIFSNGEK-----EEGRFTIHLNKA--SLHFSLHIRDSQPSDSALYLCA
TcR Vβ:       38  VTLRCKPISG----HNS-LFWYRQTMM-RGLEFLLIYFNNNVPIDDSGMPEDRFSAKMP--NASFSTLKIQPSEPRDSAVYFCA
CD4 (I):      37  VFLTCTASQK----KSIQFHWKNSNQI-KILGNQGSFLTK-GPSK---LNDRADSRRSLWD-QGNFPLLIKNLKIEDSDTYICE
CD8(Chain II):37  AKMSCEAKTFP---KGTTIYWLRELQDSNKNKHFEFLASR-TSTKGIKYGERVKKNMTLSFNSTLPFLKIMDVKPEDSGFYFCA
Poly Ig R:   151  VTLTCPFTYATR--QLKKSFYKVED----GEIVLIIDSSSKEAKDPRYKGRITLQIQST-TAKEFIVTLKHLQLNDAGQYVCQ
Consensus:        VTLTC         S          F    RQ                                   FSLTI-N   DSA-Y-CA
                                                                                                    G
                                                      V                                  I
                                                      I                                  Y     RF    L--Y
                                                      F                                  I     W  RQ Toso:        300  QRPRGSPRPRSQNNIYSACPRRARGADAAGTGEAPVPGPGAPL
FAST kinase:   2  RRPRGEPGPRA-------PRPTEGATCAGPGESWSPSPNSML
Acid SMase:    1  MPPRYGASLRQSCPRSGREQGQDGTAGAPGLLWMGLV Toso:        351  ESPWLHAPSLKTISCEYVSL
Op-IAP:      162  DAPWQQHARWYDRCEYVLL
IRS-1:       881  QQPLLRPPEPKSPGEYVNI
Acid SMase:  349  WEPWLPAFALRTLRIGGFY Toso:        372  QPAAMMEDSDSDDYINVPA
Op-IAP:      192  TEACVVRDADNEPHIERPA
IRS-1:       928  QPAPREEETGEEYMKMDL
```

FIG._3

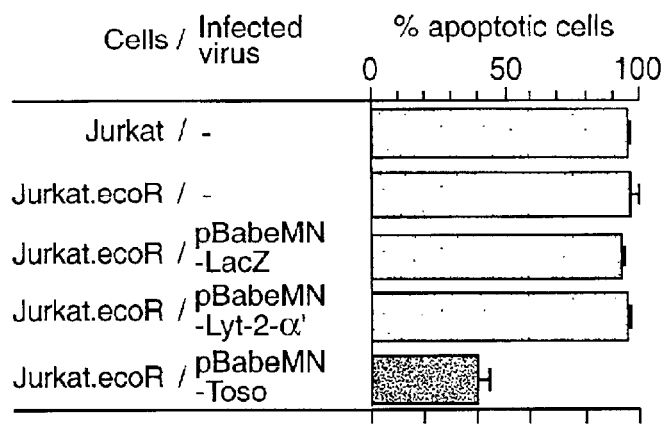
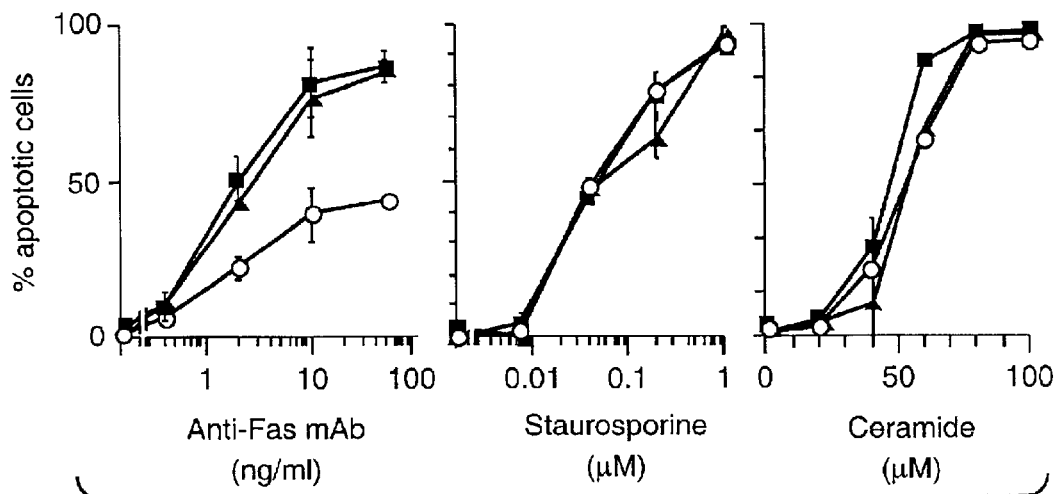
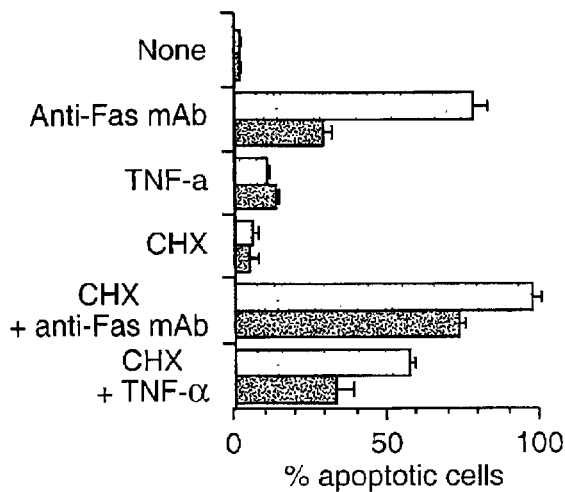
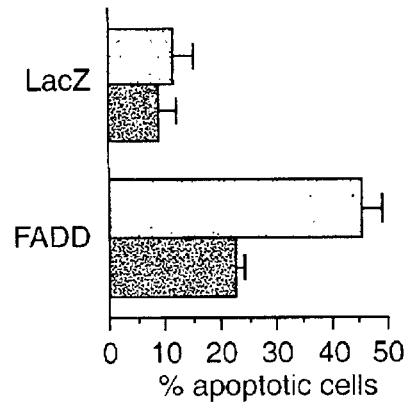
FIG._4a
FIG._4b
FIG._4c
FIG._4d

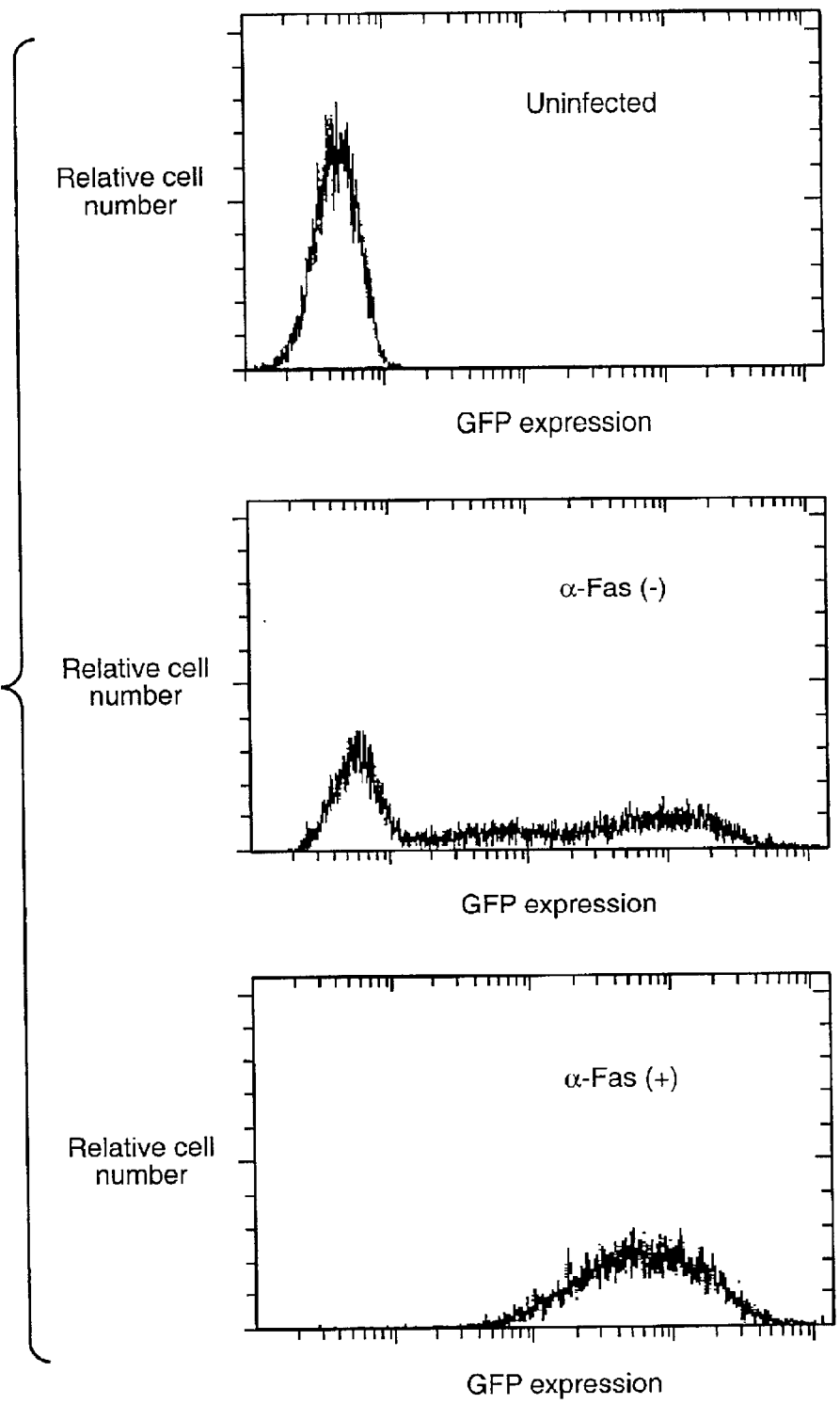
FIG._4e

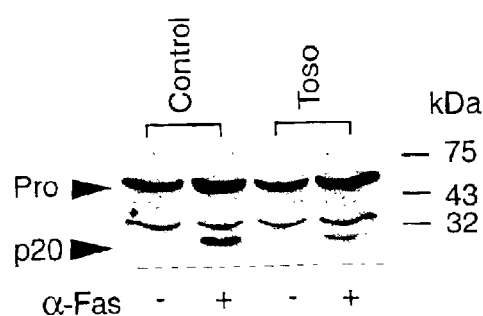
FIG._5a
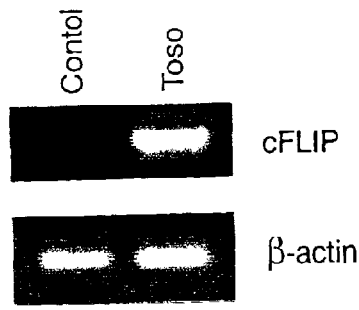
FIG._5b
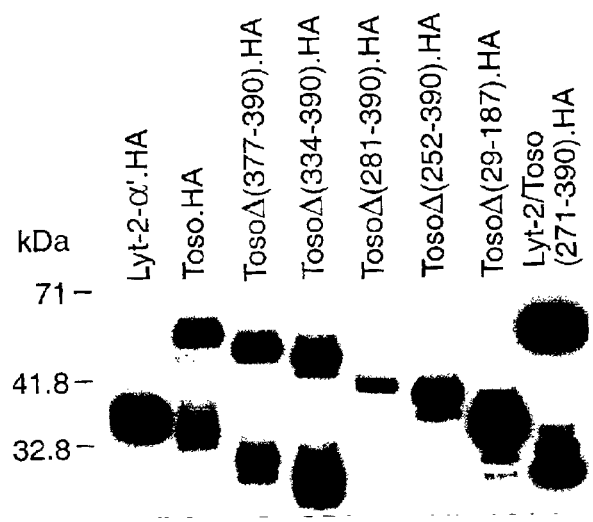
FIG._6b
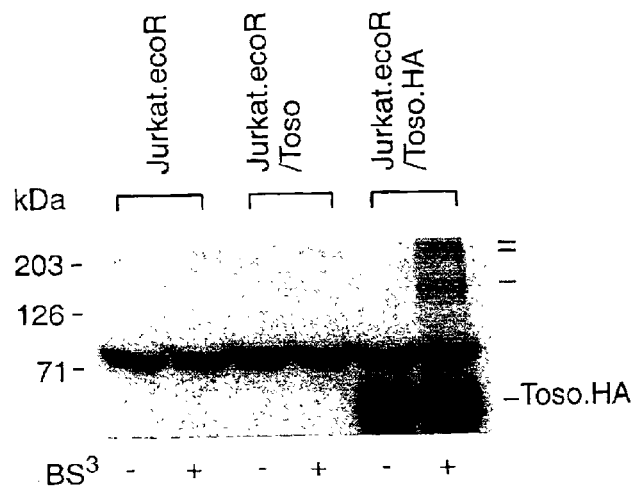
FIG._6c

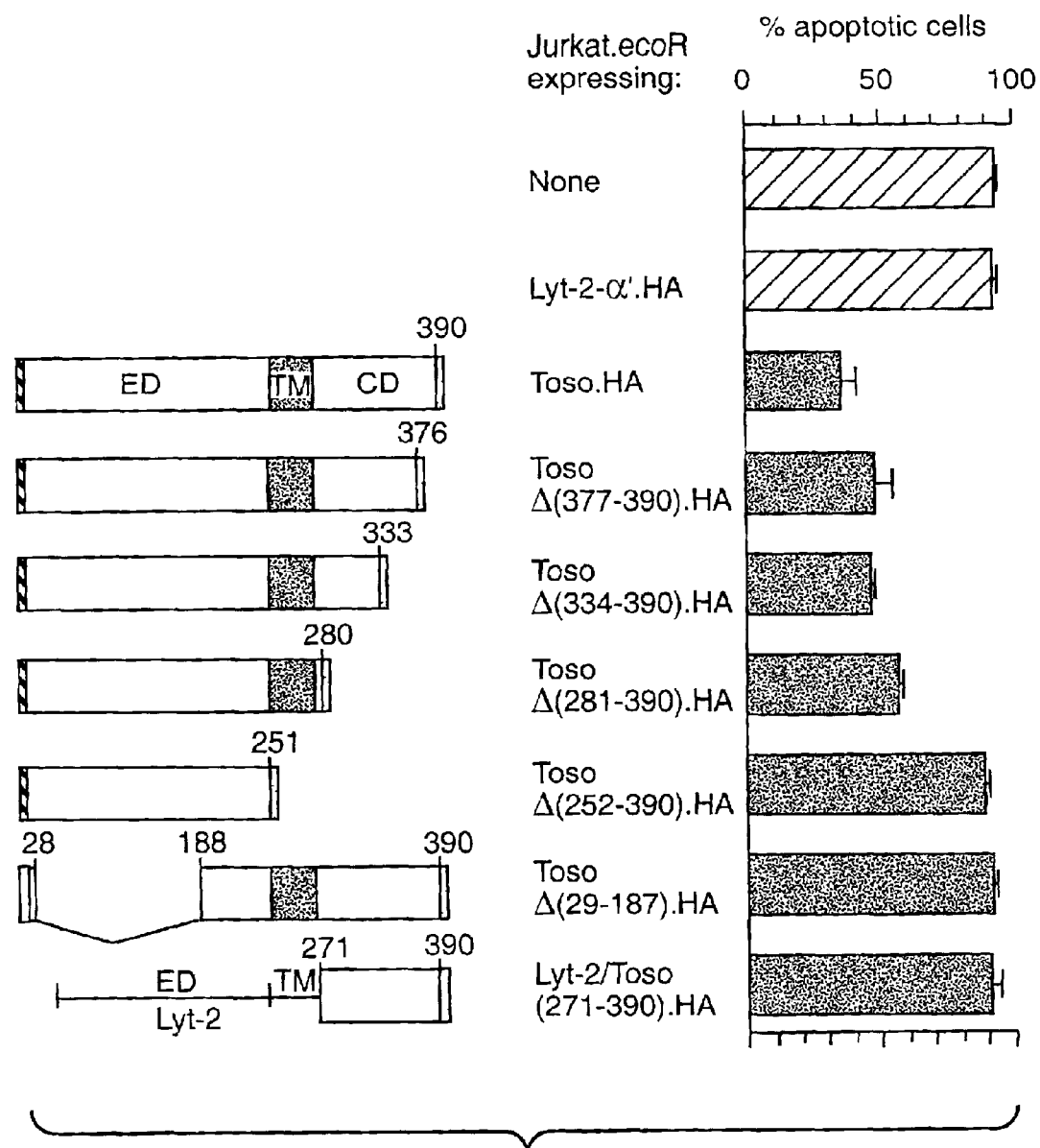
FIG._6a

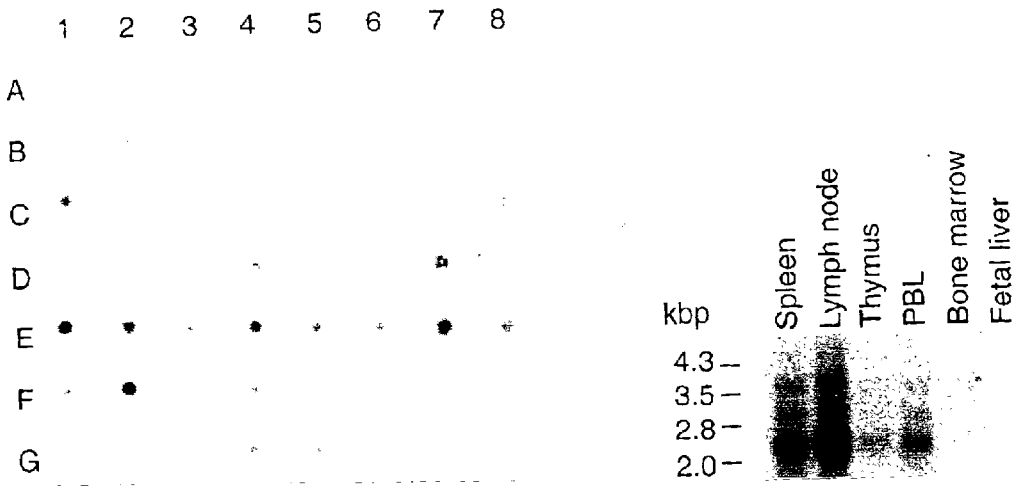
FIG._7a
FIG._7b
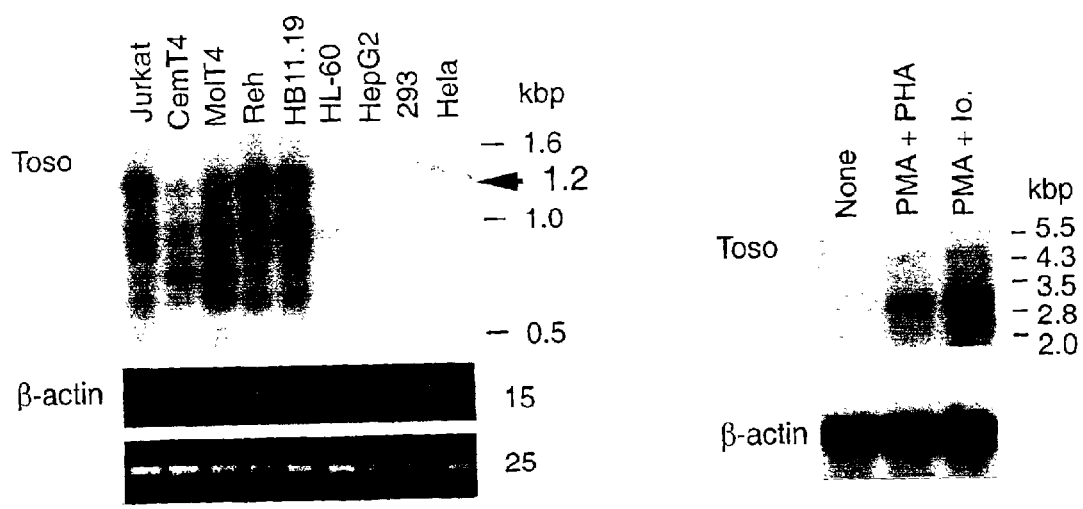
FIG._7c
FIG._8a
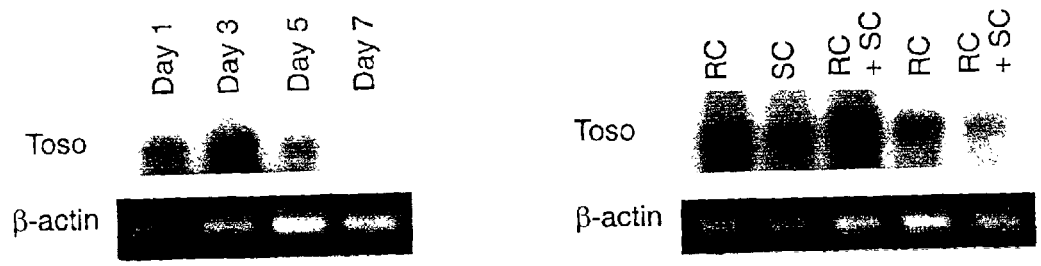
FIG._9a
FIG._9b

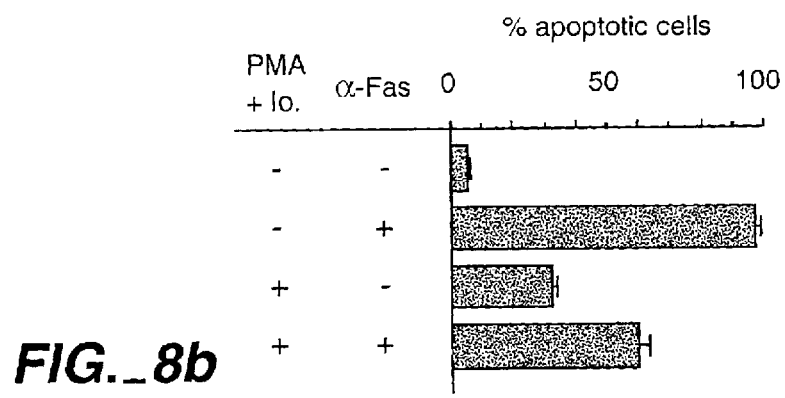
FIG._8b
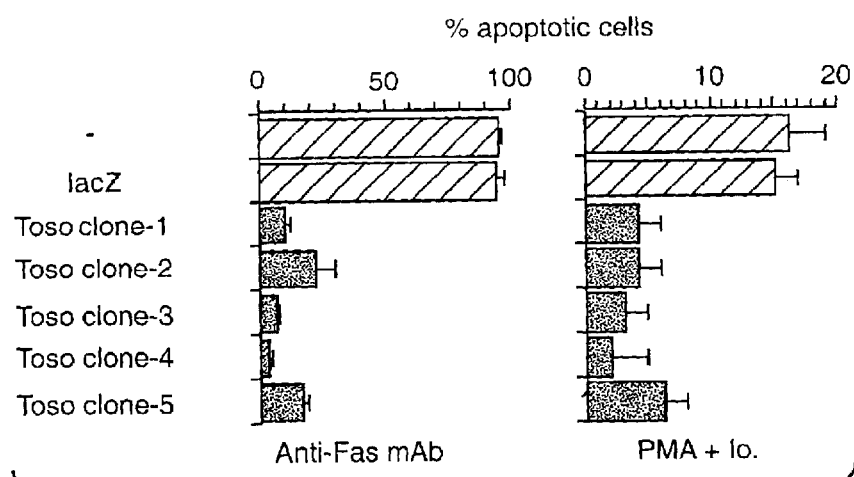
FIG._8c
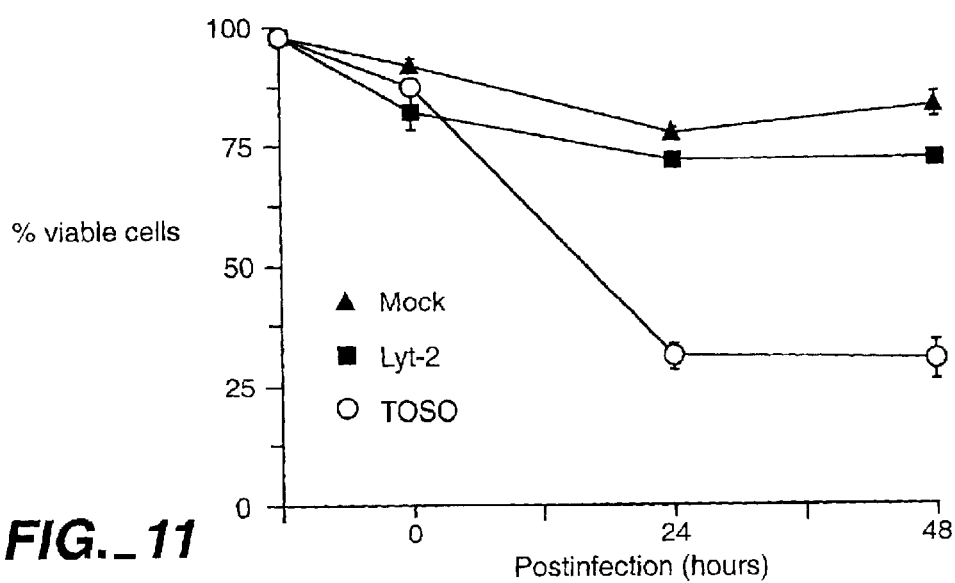
FIG._11

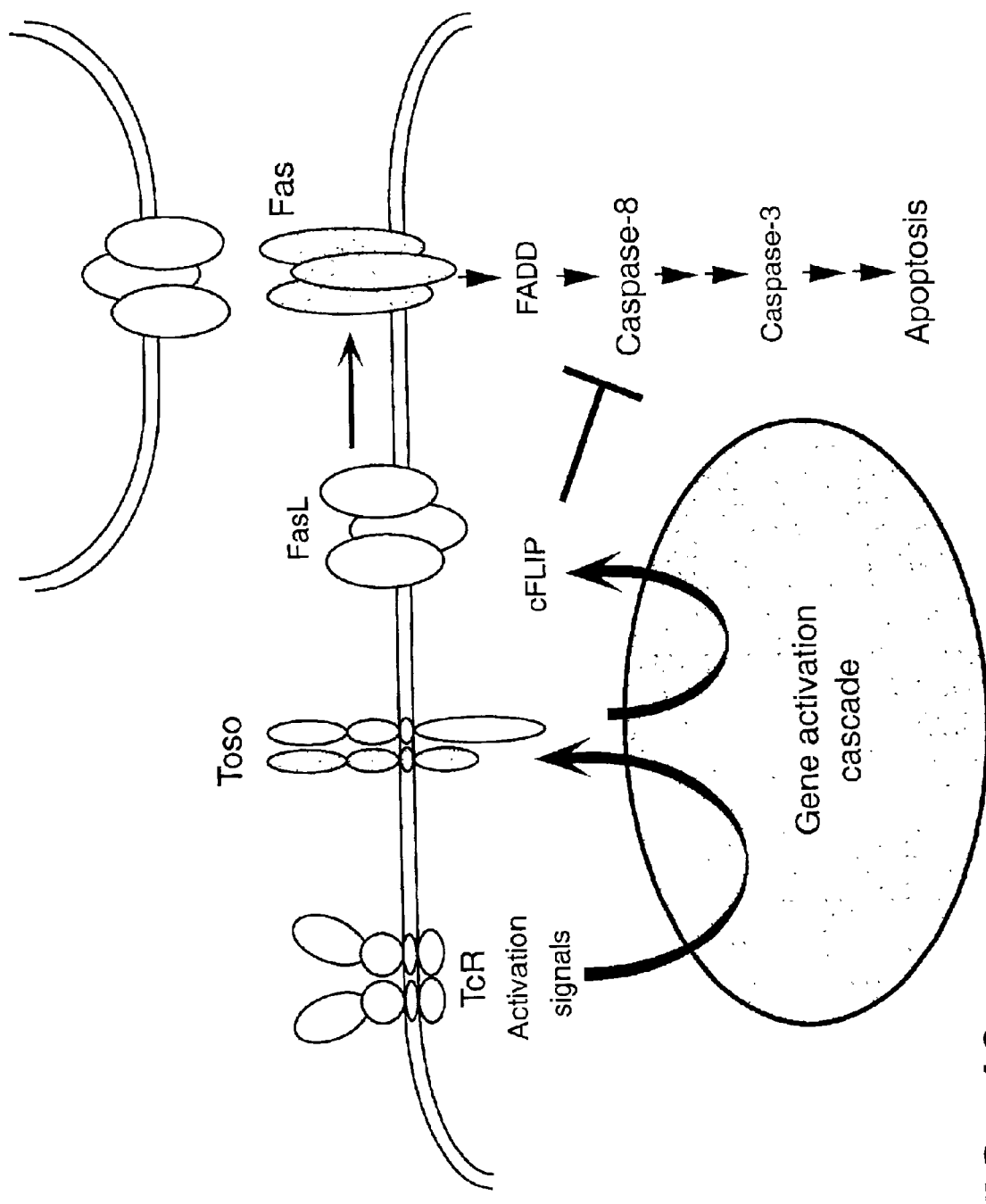
FIG._10

TOSO AS A TARGET FOR DRUG SCREENING

CROSS-REFERENCE

This patent application is a continuation of U.S. patent application Ser. No. 09/050,861, filed Mar. 30, 1998 now U.S. Pat. No. 6,555,314.

FIELD OF THE INVENTION

The invention relates to the use of Toso proteins in screening assays.

BACKGROUND OF THE INVENTION

Apoptosis or programmed cell death is an important homeostatic mechanism that maintains cell number, positioning, and differentiation. Several intracellular and intercellular processes are known to regulate apoptosis. One of the best characterized systems is initiated by the cell surface receptor, Fas (Apo-1/CD95), homologues of which initiate apoptosis in a wide range of organisms (Itoh, et al, Cell, 66:233–243 (1991); Yonehara, et al., J. Exp. Med., 169:1747–1756 (1989)). Clustering of the Fas cytoplasmic domain generates an apoptotic signal via the "death domain" (Itoh and Nagata, J. Biol. Chem., 268:10932–10937 (1993)). Several critical proteins that bind to the death domain or other domains within the cytoplasmic region have been identified using yeast two-hybrid and biochemical screens (Boldin, et al., J. Biol. Chem., 270:7795–7798 (1995); Chinnaiyan, et al, Cell, 8145:505–512 (1995); Chu, et al., Proc. Natl. Acad. Sci. USA, 92:11894–11898 (1995); Okura, et al., J. Immunol., 157:4277–4281 (1996); Sato, et al, Science. 268:411415 (1995); Stanger, et al., Cell, 8145:513–523 (1995)).

Fas engagement by Fas ligand is capable of activating the interleukin-1 β converting enzyme family of cysteine proteases (Caspases)—the proteolytic executors of apoptosis (Enari, el al, Nature, 375:78–81 (1995); Enari, et al., Nature, 380:723–726 (1996); Los, et al., Nature, 375:81–83 (1995); Tewari and Dixit, J. Biol. Chem, 270:3255–3260 (1995)). Recent studies implicate caspase8 (MACH/FLICE/Mch5) as linking Fas receptor signaling to downstream caspases via its association with FADD/MORT1 (Boldin, et al., (1995); Chinnaiyan, et al., (1995); Boldin, et al., (1996); Fernandes-Alnemri, et al., Proc. Natl. Acad. Sci. USA, 93:7464–7469 (1996); Muzio, et al., Cell, 85:817–827 (1996)). Several groups have reported that caspase-8 activation is inhibited by a cellular inhibitor, cFLIP/FLAME-1/1-FLICE (Irmler, et al., Nature 388:190–195 (1997); Srinivasula, et al., J. Biol. Chem. 272:18542–18545 (1997); Hu, et al., J. Biol. Chem., 272:17255–17257 (1997)). Other proteins involved in Fas-mediated apoptosis include: (a) the Fas-activated serine/threonine kinase (FAST kinase), which is rapidly activated during Fas-mediated apoptosis; (b) acid sphingomyelinase, which produces ceramide, a pro-apoptotic signal that acts as a second messenger in several systems; and (c) Daxx, a novel protein that links Fas to the JNK stress kinase pathway (Cifone, et al., J. Exp. Med., 180:1547–1552 (1994); Tian, et al., J. Exp. Med., 182:865–874 (1995); Yang, et al., Cell, 89:1067–1076 (1997)). The exact role of these latter co-activators has yet to be fully defined.

A balance between life and programmed cell death signals in cells is likely to be governed by multiple interacting regulators that counteract apoptotic signals with appropriate anti-apoptotic signals. Imbalances in this regulation can result in wide variety of pathologies, including cancer and immune dysfunction and it is now clear that other polypeptides besides Fas contribute to disregulation of appropriately induced apoptosis. As an example, in many tumor cell lines Fas expression does not correlate with sensitivity to Fas-induced apoptosis, implying the existence of Fas-resistance protein (Richardson, et al., Eur. J. Immunol., 24:2640–2645 (1994)). Also, in some types of cells, Fas-induced apoptosis requires protein synthesis inhibitors such as cycloheximide (Itoh and Nagata, (1993); Yonehara, et al., (1989)) and even in Fas-sensitive cells, protein synthesis inhibitors can play a synergistic role with cycloheximide (Itoh and Nagata, (1993)). These combined observations further suggest the existence of proteins capable of suppressing Fas-generated apoptotic signaling.

Additionally, in the course of a normal immune response, both cytotoxic T cell and NK cell activation can lead to Fas ligand (FasL) induction of apoptosis in target cells (Arase, et al., J. Exp. Med., 181:1235–1238 (1995); Berke, Cell, 81:9–12 (1995); Montel, et al., Cell Immunol., 166:236–246 (1995)). Although both Fas and FasL are rapidly induced following T-cell activation, activated-T cells remain resistant to Fas-induced apoptosis for several days (Klas, et al., Int. Immunol., 5:625–630 (1993); Owen-Schaub, et al., Cell Immunol., 140:197–205 (1992)). Thus, a mechanism exists to shield newly activated T cells from the cytotoxicity of their own FasL expression. This is likely to be an important component of T cell activation processes and protection in lymph nodes, splenic germinal centers and other sites at which T cell activation results in apoptosis of target cells.

Described herein is the identification and characterization of a novel surface molecule, "Toso" which is a member of the immunoglobulin gene superfamily and which specifically inhibits Fas and TNF receptor family mediated apoptosis. The results demonstrate the existence of cell surface mediated signaling pathways that lead to down is regulation of Fas-mediated apoptosis in certain cell types and suggest that activation of T cells suppresses internal signaling systems that might lead inappropriately to T cell-induced self-killing.

Accordingly, it is an object of the invention to provide Toso proteins and related molecules. It is a further object of the invention to provide recombinant nucleic acids encoding Toso proteins, and expression vectors and host cells containing the nucleic acid encoding the Toso protein. A further object of the invention is to provide methods for screening for antagonists and agonists of Toso.

SUMMARY OF THE INVENTION

In accordance with the objects outlined above, the present invention provides methods for screening for a bioactive agent capable of binding to a Toso protein encoded by a recombinant nucleic acid that will hybridize under high stringency conditions to the nucleic acid sequence depicted in FIG. 1 (SEQ ID NO:1) or its complement. The methods comprise combining a Toso protein and a candidate bioactive agent, and determining the binding of the candidate agent to the Toso protein.

In an additional aspect, the invention provides methods for screening for a bioactive agent capable of modulating the activity of a Toso cell-surface receptor, said method comprising the steps of adding a candidate bioactive agent to a cell comprising a recombinant nucleic acid encoding a Toso receptor, exposing the cells to an apoptotic agent that will induce apoptosis, and determining the effect of the candidate bioactive agent on apoptosis.

In a further aspect, the invention provides methods of modulating apoptosis in a cell comprising administering to the cell an exogenous compound that binds to a Toso protein wherein the binding modulates the biological activity of said Toso protein.

In an additional aspect, the invention provides methods for identifying a cell containing a mutant Toso gene comprising determining the sequence of all or part of at least one of the endogenous Toso genes. Similarly, methods of identifying the Toso genotype of an individual are provided.

In a further aspect, the invention provides methods for diagnosing an apoptosis related condition in an individual. The activity of Toso in a tissue from a first individual is measured and compared to the activity of Toso in a tissue from a second, unaffected individual or from a second tissue in the first individual. When the activity of Toso from said first individual is less than the activity of Toso in the second individual, the first individual is at risk for an apoptosis related condition.

BRIEF DESCRIPTION OF THE DRAWINGS

FIG. 1 depicts the nucleotide sequence (SEQ ID:NO 1) of Toso. Also presented are the positions of the initiator ATG start codon, the stop codon the nucleotides which correspond to the signal sequence and the nucleotides which correspond to the putative transmembrane domain of the Toso protein.

FIG. 2a depicts the amino acid sequence (SEQ ID:NO 2) of amino acids 1 to 390 deduced from nucleotides 1 to 1173 of the nucleotide sequence shown in FIG. 1 (SEQ ID:NO 1). Two hydrophobic regions are underlined.

FIG. 2b depicts a Kyte-Dolittle hydropathy plot analysis of Toso gene product (upper) and schematic presentation of Toso (bottom). The mature Toso is a 390-amino acid protein with the leader sequence of 17 amino acids (hatched bar), the extracellular domain of 236 amino acids (ED), the transmembrane region of 19 amino acids (TM; dotted bar) and the cytoplasmic domain of 118 amino acids (CD). The immunoglobulin domain (Ig), the basic amino acid-rich region (Basic), the proline-rich region (Proline), and the acidic amino acid-rich region (Acidic) are indicated.

FIG. 3 (SEQ ID NOS3–21) depicts BLAST search results using the Toso gene product. The position of the first amino acid in each sequence is given in the left side of the alignment. Gaps are indicated by dashes. Dark and light shading refer to identical and similar residues, respectively. For sequence alignment of the Toso N-terminus. IgVH (GIHUNM), IgVλ(LIMS4E), TcR Vα(RWMSAV), TCR Vβ(RWHUVY), CD4 (U47924), CD8 chain 11 (X04310), Poly Ig R (QRRBG) and immunoglobulin V-set consensus sequence are shown in the alignment. Arrows indicate positions characteristic of many V-set sequences. The sequence of the Toso cytoplasmic domain is aligned with acid sphingomyelinase, insulin receptor substrate 1 (IRS-1) and apoptosis inhibitor, IAP, from *Orgyia pseudotsugata* nuclear polyhedrosis virus (Op-IAP).

FIG. 4a depicts the effect of Toso on anti-Fas induced apoptosis. The percentage of apoptotic cells are expressed as the mean (hatched and shaded bar)±SD of triplicate cultures. Apoptotic cells in each culture without anti-Fas mAb were less than 2%.

FIG. 4b depicts the effect of Toso on anti-Fas-, staurosporine- and ceramide-induced apoptosis in Jurkat.ecOR cells (closed triangle), Jurkat.ecOR cells infected with pBabeMN-lacZ (closed square) and pBabeMN-Toso (open circle). The percentage of apoptotic cells are expressed as the mean (symbol)±SD (vertical bar) of triplicate cultures.

FIG. 4c depicts the effect of Toso on FADD-induced apoptosis in Jurkat.ecOR cells infected with pBabeMN-Lyt-2-α'(hatched bar), and pBabeMN-Toso (shaded bar). The percentage of apoptotic cells are expressed as the mean (hatched bar or shaded bar)±SD of triplicate cultures.

FIG. 4d depicts the effect of Toso on TNF-α-induced apoptosis in Jurkat.ecOR cells. The percentage of apoptotic cells are expressed as the mean (hatched bar or shaded bar)±SD of triplicate cultures.

FIG. 4e depicts the effect Toso on anti-Fas mAb-induced apoptosis in cells cultured with (α-Fas (+)) or without (α-Fas (−)) 50 ng/ml of anti-Fas mAb. After culture for five days, GFP expression of survived cells were analyzed by FACScan.

FIG. 5a depicts the results of Western blot analysis of caspase-8 processing by induction of cFLIP. Jurkat.ecOR cells (control) and pBabeMN-Toso-infected Jurkat.ecOR cells (Toso) were cultured with (+) or without (−) 50 ng/ml of anti-Fas mAb (α-Fas) for 6 hours.

Positions of pro-caspase-8 (Pro), the processed form (p20) and standard marker are indicated.

FIG. 5b depicts the results of RT-PCR of cFLIP expression in Jurkat.ecOR cells (control) and pBabeMN-Toso-infected Jurkat.ecOR cells (Toso).

FIG. 6a depicts the effect of Toso deletion mutant expression on anti-Fas mAb-induced apoptosis. Structure of the Toso deletion mutants is shown at the left side of this panel. Full-length Toso is a 390-amino acid protein with the leader sequence of 17 amino acids (hatched bar), the extracellular domain of 236 amino acids (ED), the transmembrane region of 19 amino acids (TM; dark-shaded bar) and the cytoplasmic domain of 118 amino acids (CD). The hemagglutinin (HA) tag is indicated as a light shaded bar. The percentage of apoptotic cells is expressed as the mean (hatched and shaded bar)±SD of triplicate cultures.

FIG. 6b depicts Western blot analysis of deletion mutants using anti-HA antibody. The molecular weight of major products from Toso.HA, TosoΔ(377–390).HA, TosoΔ (334–390). HA, TosoΔ (252–390). HA, TosoΔ (281–390). HA, TosoΔ (29–187). HA and Lyt-2/Toso(271–390).HA was 60/35, 55/30, 50/26, 40, 38, 35, 60/30 kDa, respectively. Positions and sizes (kDa) of standard protein markers are indicated in left side of panel.

FIG. 6c depicts Crosslinking the extracellular domain of Toso. Positions of standard protein markers and Toso.HA are indicated in left side and right of panel, respectively.

FIG. 7a depicts mRNA dot blot analysis of Toso gene in several human tissues.

FIG. 7b depicts Northern blot analysis of Toso gene in several human immune tissues. Positions and sizes (kbp) of Toso mRNA are indicated in left side of panels.

FIG. 7c depicts RT-PCR analysis of Toso in human cell lines (upper panel). Positions and sizes (kbp) of Toso and standard nucleotide makers are indicated. As a control for loading, we amplified β-actin cDNA (lower panels).

FIG. 8a depicts (a) Northern blot analysis of Toso gene in Jurkat cells (None) and Jurkat cells stimulated with PMA and PHA (PMA+PHA) or PMA and Ionomycin (PMA+Io.). RNA was electrophoresed, transferred to a Hybond N+membrane and hybridized with a radiolabelled probe specific for Toso (upper) and β-actin (lower). Film was exposed at −70° C. with an intensifying screen for two days (upper). Positions and sizes (kbp) of Toso mRNA are indicated in right side of panels.

FIG. 8b depicts activation induced resistance to anti-Fas mAb-induced apoptosis in Jurkat cells. The percentage of apoptotic cells are expressed as the mean (hatched bar)±SD of triplicate cultures.

FIG. 8c depicts the effect of Toso on PMA and Ionomycin (PMA+Io.)-induced apoptosis. Jurkat.ecOR cells (−), Jurkat.ecOR cells infected with pBabeMN-lacZ (lacZ), pBabeMN-Toso-infected clones (Toso clones 1–5) were cultured with 10 ng/ml of anti-Fas mAb (left), 10 ng/ml PMA and 500 ng/ml Ionomycin (right) for 24 hours. The percentage of apoptotic cells are expressed as the mean (hatched bar and shaded bar)±SD of triplicate cultures.

FIG. 9a depicts the RT-PCR analysis of Toso in peripheral blood mononuclear cells after activation with PHA (upper panel, the 1.2 kbp fragment of Toso).

FIG. 9b depicts analysis of Toso in peripheral blood mononuclear cells after allogenic stimulation (upper panel, the 1.2 kbp fragment of Toso). Stimulator cells (SC), responder cells (RC) or mixed cells (RC+SC) were cultured for one day (day 1) and six days (day 6).

FIG. 10 depicts a model for the role of Toso in T cell activation. In the model, the role of Toso is to be induced following T cell activation and to protect T cells from self-induced programmed cell death. The inhibitory effects of Toso on Fas signaling maps at the level of caspase-8 through induced expression of cFLIP.

FIG. 11 depicts massive cell death of 70 Z/3 cells induced by TOSO. 70Z/3 cells were incubated with supernatant from φNX-E (closed triangle), viral supernatant of pBabeMN-Lyt-2α (closed square), or pBabeMN-TOSO (open circle) for 12 hours including the initial spinning at 2500 rpm for 90 min. Infection frequency of pBabeMN-Lyt-2α was determined to be 79% at 48 hours post infection. The percentage of viable cells at various time points are expressed as mean (symbol)±SD (vertical bar) of triplicate cultures.

DETAILED DESCRIPTION OF THE INVENTION

The present invention provides novel Ig domain-containing Toso polypeptides, with potent pathway-specific anti-apoptotic effects in hematopoietic cells. Toso (named after a Japanese liquor that is drunk on New Year's Day to celebrate long life and eternal youth) exerts an inhibitory activity against apoptosis induced by Fas-, TNF-α-, FADD and PMA/Ionomycin but not against staurosporine- or ceramide-induced apoptosis. Without being bound by theory, the mechanism of blocking apoptotic activation, and the pathway specificity of the effect, is most likely explained by Toso induction of cFLIP expression which inhibits caspase-8 processing. Toso is expressed within lymphoid tissues and hematopoietic cells, and is enhanced after T-cell activation. These results suggest that Toso plays an important role in the immune system. Surprisingly, Toso also displays pro-apoptotic effects; Toso promoted cell death in the murine preB cell line, 70Z/3 cells, an effect that is shown to be caused by the cytoplasmic domain.

Accordingly, the present invention provides Toso proteins and nucleic acids. In a preferred embodiment, the Toso proteins are from vertebrates and more preferably from mammals including dogs, cats and rabbits, rodents (including rats, mice, hamsters, guinea pigs, etc.), primates (including chimpanzees, African green monkeys, etc.), farm animals (including sheep, goats, pigs, cows, horses, etc.) and in the most preferred embodiment, from humans. However, using the techniques outlined below, Toso proteins from other organisms may also be obtained.

As outlined herein, the Toso proteins of the present invention are Ig superfamily molecules which are expressed in a variety of tissue types, including, but not limited to lymph nodes, peripheral blood leukocytes, thymus, lung, and kidney. As further outlined herein, Toso proteins exert pathway specific anti-apoptotic effects in hematopoietic cells. Toso is a membrane bound protein, as it contains a putative transmembrane domain. The extracellular domain of Toso has homology to immunoglobulin variable domains.

A Toso protein of the present invention may be identified in several ways. "Protein" in this sense includes proteins, polypeptides, and peptides. A Toso nucleic acid or Toso protein is initially identified by substantial nucleic acid and/or amino acid sequence homology to the sequences shown in FIGS. 1 and 2a. Such homology can be based upon the overall nucleic acid or amino acid sequence.

As used herein, a protein is a "Toso protein" if the overall homology of the protein sequence to the amino acid sequence shown in FIG. 2a (SEQ ID NO:2) is preferably greater than about 50 or 60%, more preferably greater than about 70 or 75%, even more preferably greater than about 80% and most preferably greater than 85%. In some embodiments the homology will be as high as about 90 to 95 or 98%. Homology in this context means sequence similarity or identity, with identity being preferred. Identical in this context means identical amino acids at corresponding positions in the two sequences which are being compared. Homology in this context includes amino acids which are identical and those which are similar (functionally equivalent). This homology will be determined using standard techniques known in the art, such as the Best Fit sequence program described by Devereux, et al., *Nucl. Acid Res.*, 12:387–395 (1984), preferably using the default settings, or the BLASTX program (Altschul, et al., *J. Mol. Biol.*, 215:403410 (1990)). The alignment may include the introduction of gaps in the sequences to be aligned. In addition, for sequences which contain either more or fewer amino acids than the proteins shown in the Figures, it is understood that the percentage of homology will be determined based on the number of homologous amino acids in relation to the total number of amino acids. Thus, for example, homology of sequences shorter than that shown in the Figures, as discussed below, will be determined using the number of amino acids in the shorter sequence.

As outlined herein, Toso proteins have several important domains. Toso contains a cytoplasmic domain from amino acids 273 to 390, with the extracellular domain spanning from 18 to 253 (unless otherwise specified, all amino acid numbering is based on the human sequence). Toso contains a standard transmembrane domain, spanning from amino acids 254 to 272. Toso contains an additional hydrophobic region at the N-terminus, amino acids 1 to 17, corresponding to a putative signal sequence. In addition, the cytoplasmic domain of Toso contains a basic amino acid-rich region (from Arg274 to Arg323), a proline rich region (from Pro334 to P346), and an acidic amino acid-rich region (from Glu378 to Asp384). In addition, the cytoplasmic domain has partial homology to FAST kinase, acid sphingomyleinase, insulin receptor substrate-1 (IRS-1) and the apoptosis inhibitor from *Orgyia pseudotsugata* nuclear polyhedrosis virus (Op-IAP). The extracellular domain of Toso has homology to the immunoglobulin V-region.

As used herein, a protein is also a "Toso protein" if the homology of the cytoplasmic domain comprising amino acids 273 to 390, or the extracellular domain comprising amino acids 18 to 253, respectively, of the amino acid sequence shown in FIG. 2a (SEQ ID NO:2) is preferably greater than about 50% of 60%, more preferably greater than about 70% or 75%, even more preferably greater than about 80% and most preferably greater than 85%. In some embodiments the homology will be as high as about 90 to 95 or 98%.

Toso proteins of the present invention may be shorter or longer than the amino acid sequences shown in the Figures. Thus, in a preferred embodiment, included within the definition of Toso proteins are portions or fragments of the sequences depicted in the Figures. As outlined herein, Toso deletion mutants can be made, including, but not limited to, the deletion of amino acids 377–390, 334–390, 281–390, 252–390, and 29–187. As further outlined herein, Toso fusion proteins can be made including, but not limited to, the fusion of amino acids 1–271. A preferred Toso fragment is the cytoplasmic domain of Toso, which may modulate apoptosis, as shown herein. A further preferred Toso fragment is the extracellular domain of Toso, comprising roughly the first 236 amino acids of Toso, which is required for the anti-apoptotic effects on anti-Fas antibody-stimulated cells. However, as outlined herein, preferred fragments of Toso also include a transmembrane domain, as it may be involved in signaling and Fas-induced apoptosis by Toso may require its insertion into membranes.

Thus, in a preferred embodiment, the Toso proteins of the present invention are Toso polypeptides. In this embodiment, a Toso polypeptide comprises at least the immunoglobin V-like domain, and preferably a transmembrane domain, although it may contain additional amino acids as well. As shown in the Examples and discussed below, Toso is an Ig superfamily protein which is capable of inhibiting apoptosis mediated by members of the Fas or TNF receptor family of proteins.

In a preferred embodiment, the Toso proteins are derivative or variant Toso proteins. That is, as outlined more fully below, the derivative Toso peptide will contain at least one amino acid substitution, deletion or insertion, with amino acid substitutions being particularly preferred. The amino acid substitution, insertion or deletion may occur at any residue within the Toso peptide. As outlined below, particularly preferred substitutions are made within the extracellular domain or cytoplasmic domain of the Toso protein.

In addition, as is more fully outlined below, Toso proteins can be made that are longer than those depicted in the figures, for example, by the addition of epitope or purification tags, the addition of other fusion sequences, etc.

Toso proteins may also be identified as being encoded by Toso nucleic acids. Thus, Toso proteins are encoded by nucleic acids that will hybridize to the sequence depicted in FIG. 1 (SEQ ID NO:1), or its complement, as outlined herein.

In a preferred embodiment, when the Toso protein is to be used to generate antibodies, the Toso protein must share at least one epitope or determinant with the full length protein shown in FIG. 2a (SEQ ID NO:2). By "epitope" or "determinant" herein is meant a portion of a protein which will generate and/or bind an antibody. Thus, in most instances, antibodies made to a smaller Toso protein will be able to bind to the full length protein. In a preferred embodiment, the epitope is unique; that is, antibodies generated to a unique epitope show little or no cross-reactivity. In a preferred embodiment, the antibodies are generated to an extracellular portion of the Toso molecule, i.e. to all or some of the N-terminal region from amino acid numbers 18–253.

In a preferred embodiment, the antibodies to Toso are capable of reducing or eliminating the biological function of Toso, as is described below. That is, the addition of anti-Toso antibodies (either polyclonal or preferably monoclonal) to cells comprising Toso receptors may reduce or eliminate the Toso receptor activity, blocking the signaling pathway that blocks apoptosis; that is, when Toso receptor function is reduced or eliminated, the cells die. Generally, at least a 50% decrease in activity is preferred, with at least about 75% being particularly preferred and about a 95–100% decrease being especially preferred.

The Toso antibodies of the invention specifically bind to Toso proteins. By "specifically bind" herein is meant that the antibodies bind to the protein with a binding constant in the range of at least $10^6$–$10^8$ M, with a preferred range being $10^7$–$10^9$ M.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of FIG. 1 (SEQ ID NO:1) is preferably greater than 50 or 60%, more preferably greater than about 70 to 75%, particularly greater than about 80% and most preferably greater than 85%. In some embodiments the homology will be as high as about 90 to 95 or 98%.

In a preferred embodiment, a Toso nucleic acid encodes a Toso protein. As will be appreciated by those in the art, due to the degeneracy of the genetic code, an extremely large number of nucleic acids may be made, all of which encode the Toso proteins of the present invention. Thus, having identified a particular amino acid sequence, those skilled in the art could make any number of different nucleic acids, by simply modifying the sequence of one or more codons in a way which does not change the amino acid sequence of the Toso.

In one embodiment, the nucleic acid homology is determined through hybridization studies. Thus, for example, nucleic acids which hybridize under high stringency to the nucleic acid sequences shown in FIG. 1 (SEQ ID NO:1) or its complement is considered a Toso gene. High stringency conditions are known in the art; see for example Maniatis, et al., *Molecular Cloning: A Laboratory Manual,* 2d Edition (1989), and Short Protocols in Molecular Biology, ed. Ausubel, et al., both of which are hereby incorporated by reference. An example of such conditions includes hybridization at about 42° C. in about 6×SSC with 50% formamide and washing conditions of about 65° C. in about 0.2×SSC, 0.1×SDS.

In another embodiment, less stringent hybridization conditions are used; for example, moderate or low stringency conditions may be used, as are known in the art; see Maniatis and Ausubel, supra. An example of such conditions includes hybridization at about 50 to 55° C. in 5×SSPE and washing conditions of about 50° C. in about 5×SSPE.

The Toso proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 1 also includes the complement of the sequence. By the term "recombinant nucleic acid" herein is meant nucleic acid, originally formed in vitro, in general, by the manipulation of nucleic acid by endonucleases, in a form not normally found in nature. Thus an isolated Toso nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a Toso protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

Once identified, the polypeptides comprising the biologically active sequences may be prepared in accordance with conventional techniques, such as synthesis (for example, use of a Beckman Model 990 peptide synthesizer or other commercial synthesizer).

Also included within the definition of Toso proteins of the present invention are amino acid sequence variants. These variants fall into one or more of three classes: substitutional, insertional or deletional variants. These variants ordinarily are prepared by site specific mutagenesis of nucleotides in the DNA encoding the Toso protein, using cassette or PCR mutagenesis or other techniques well known in the art, to produce DNA encoding the variant, and thereafter expressing the DNA in recombinant cell culture as outlined above. However, variant Toso protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the Toso protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not to be predetermined. For example, in order to optimize the performance of a mutation at a given site, random mutagenesis may be conducted at the target codon or region and the expressed Toso variants screened for the optimal combination of desired activity. Techniques for making substitution mutations at predetermined sites in DNA having a known sequence are well known, for example, M13 primer mutagenesis and PCR mutagenesis. Screening of the mutants is done using assays of Toso protein activities; for example, for binding domain mutations, competitive binding studies such as are outlined in the Examples may be done.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger. For example, a preferred variant comprises the deletion of the cytoplasmic domain, leaving only the extracellular domain of Toso, preferably including the transmembrane domain. Additional preferred variants comprise the cytoplasmic domain alone or a soluble receptor (i.e. the extracellular domain lacking the transmembrane domain).

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the Toso protein are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the Toso proteins as needed. Alternatively, the variant may be designed such that the biological activity of the Toso protein is altered. For example, glycosylation sites, and more particularly one or more O-linked or N-linked gylcosylation sites may be altered or removed. Either or both of the transmembrane domains may be altered or removed, to make a soluble or secreted protein, i.e. the extracellular domain.

Covalent modifications of Toso polypeptides are included within the scope of this invention. One type of covalent modification includes reacting targeted amino acid residues of a Toso polypeptide with an organic derivatizing agent that is capable of reacting with selected side chains or the N-or C-terminal residues of a Toso polypeptide. Derivatization with bifunctional agents is useful, for instance, for crosslinking Toso to a water-insoluble support matrix or surface for use in the method for purifying anti-Toso antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, *Proteins: Structure and Molecular Properties*. W. H. Freeman & Co., San Francisco, pp. 79–86 (1983)], acetylation of the N-terminal amine, and amidation of any C-terminal carboxyl group.

Another type of covalent modification of the Toso polypeptide included within the scope of this invention comprises altering the native glycosylation pattern of the polypeptide. "Altering the native glycosylation pattern" is intended for purposes herein to mean deleting one or more carbohydrate moieties found in native sequence Toso polypeptide, and/or adding one or more glycosylation sites that are not present in the native sequence Toso polypeptide.

Addition of glycosylation sites to Toso polypeptides may be accomplished by altering the amino acid sequence thereof. The alteration may be made, for example, by the addition of, or substitution by, one or more serine or threonine residues to the native sequence Toso polypeptide (for O-linked glycosylation sites). The Toso amino acid sequence may optionally be altered through changes at the DNA level, particularly by mutating the DNA encoding the Toso polypeptide at preselected bases such that codons are generated that will translate into the desired amino acids.

Another means of increasing the number of carbohydrate moieties on the Toso polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259–306 (1981).

Removal of carbohydrate moieties present on the Toso polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge, et al., *Anal. Biochem.*, 118:131 (1981). Enzymatic cleavage of carbohydrate moieties on polypeptides can be achieved by the use of a variety of endo-and exo-glycosidases as described by Thotakura, et al., *Meth. Enzymol.*, 138:350 (1987).

Another type of covalent modification of Toso comprises linking the Toso polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337.

Toso polypeptides of the present invention may also be modified in a way to form chimeric molecules comprising a Toso polypeptide fused to another, heterologous polypeptide or amino acid sequence. In one embodiment, such a chimeric molecule comprises a fusion of a Toso polypeptide with a tag polypeptide which provides an epitope to which an anti-tag antibody can selectively bind. The epitope tag is generally placed at the amino-or carboxyl-terminus of the Toso polypeptide. The presence of such epitope-tagged forms of a Toso polypeptide can be detected using an antibody against the tag polypeptide. Also, provision of the epitope tag enables the Toso polypeptide to be readily purified by affinity purification using an anti-tag antibody or another type of affinity matrix that binds to the epitope tag. In an alternative embodiment, the chimeric molecule may comprise a fusion of a Toso polypeptide with an immunoglobulin or a particular region of an immunoglobulin. For a bivalent form of the chimeric molecule, such a fusion could be to the Fc region of an IgG molecule or GST fusions.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field, et al., *Mol. Cell Biol.*, 8:2159–2165 (1988)]; the c-myc tag and the 8F9, 3C7, 6E10, G4, B7, and 9E10 antibodies thereto [Evan, et al., *Molecular and Cellular Biology* 5:3610–3616 (1985)]; and the Herpes Simplex virus glycoprotein D (gD) tag and its antibody [Paborsky, et al., *Protein Engineering*, 3(6):547–553 (1990)]. Other tag polypeptides include the Flag-peptide [Hopp, et al., *BioTechnology*, 6:1204–1210 (1988)]; the KT3 epitope peptide [Martin, et al., *Science*, 255:192–194 (1992)]; tubulin epitope peptide [Skinner, et al., *J. Biol. Chem.*, 266:15163–15166 (1991)]; and the T7 gene 10 protein peptide tag [Lutz-Freyermuth, et al., *Proc. Natl. Acad. Sci. USA*, 87:6393–6397 (1990)].

Also included with the definition of Toso protein are other Toso proteins of the Toso family, and Toso proteins from other organisms, which are cloned and expressed as outlined below. Thus, probe or degenerate polymerase chain reaction (PCR) primer sequences may be used to find other related Toso proteins from humans or other organisms. As will be appreciated by those in the art, particularly useful probe and/or PCR primer sequences include the unique areas of the Toso nucleic acid sequence. Thus, useful probe or primer sequences may be designed to: all or part of the sequence of the immunoglobulin V-like Toso domain, all or part of the unique extracellular domain, which spans roughly amino acids 18–253, or sequences outside the coding region. As is generally known in the art, preferred PCR primers are from about 15 to about 35 nucleotides in length, with from about 20 to about 30 being preferred, and may contain inosine as needed. The conditions for the PCR reaction are well known in the art.

Once the Toso nucleic acid is identified, it can be cloned and, if necessary, its constituent parts recombined to form the entire Toso nucleic acid. Once isolated from its natural source, e.g., contained within a plasmid or other vector or excised therefrom as a linear nucleic acid segment, the recombinant Toso nucleic acid can be further-used as a probe to identify and isolate other Toso nucleic acids. It can also be used as a "precursor" nucleic acid to make modified or variant Toso nucleic acids and proteins.

Using the nucleic acids of the present invention which encode a Toso protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the Toso protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the Toso protein; for example, transcriptional and translational regulatory nucleic acid sequences from *Bacillus* are preferably used to express the Toso protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

The Toso proteins of the present invention are produced by culturing a host cell transformed with an expression vector containing nucleic acid encoding a Toso protein, under the appropriate conditions to induce or cause expression of the Toso protein. The conditions appropriate for Toso protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells, for example primary cells, including stem cells, including, but not limited to bone marrow stem cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines, Jukat cells, human cells and other primary cells.

In a preferred embodiment, the Toso proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for Toso protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, the CMV promoter, a retroviral LTR promoter, mouse maloney luekemia virus LTR, or pBabeMN.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, Toso proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of Toso protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the Toso protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans*, among others.

The bacterial expression vectors are transformed into bacterial host cells using techniques well known in the art, such as calcium chloride treatment, electroporation, and others.

In one embodiment, Toso proteins are produced in insect cells. Expression vectors for the transformation of insect cells, and in particular, baculovirus-based expression vectors, are well known in the art.

In a preferred embodiment, Toso protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The Toso protein may also be made as a fusion protein, using techniques well known in the art. Thus, for example, for the creation of monoclonal antibodies, if the desired epitope is small, the Toso protein may be fused to a carrier protein to form an immunogen. Alternatively, the Toso protein may be made as a fusion protein to increase expression, or for other reasons. For example, when the Toso protein is a Toso peptide, the nucleic acid encoding the peptide may be linked to other nucteic acid for expression purposes.

In one embodiment, the Toso nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the Toso protein is purified or isolated after expression. Toso proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the Toso protein may be purified using a standard anti-Toso antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the Toso protein. In some instances no purification will be necessary.

Once expressed and purified if necessary, the Toso proteins and nucleic acids are useful in a number of applications.

In a preferred embodiment, modified Toso cell-surface receptors, and cells containing the modified receptors, are made. In one embodiment, non-human animals preferably transgenic) are made that contain modified Toso receptors; similarly, "knock-out" animal models and Toso transgenic animals that contain an inducible promoter may be made.

In a preferred embodiment, the Toso proteins, nucleic acids, modified receptors and cells containing the native or modified receptors are used in screening assays. Identification of this important receptor permits the design of drug screening assays for compounds that modulate Toso receptor activity.

Screens may be designed to first find candidate agents that can bind to Toso receptors, and then these agents may be used in assays that evaluate the ability of the candidate agent to modulate Toso activity. Thus, as will be appreciated by those in the art, there are a number of different assays which may be run; binding assays and activity assays. Of particular importance in these embodiments is that the extracellular portion of Toso is mainly responsible for the anti-apoptotic effects. Accordingly, candidate agents may be added directly to cells without the need to target the agents intracellularly when assaying for anti-apoptotic effects. Of further importance is that the cytoplasmic domain of Toso has been shown to enhance apoptosis. Accordingly, both the extracellular and cytoplasmic domains of Toso may be used independently as a basis for binding assays.

Thus, in a preferred embodiment, the methods comprise combining a Toso cell surface receptor and a candidate bioactive agent, and determining the binding of the candidate agent to the Toso receptor. Preferred embodiments utilize the human Toso cell surface receptor (or portions, as outlined herein, such as the extracellular domain or the cytoplasmic domain), although other mammalian receptors may also be used in either case, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, variant or derivative Toso receptors may be used, including deletion Toso receptors as outlined above.

Furthermore, included within the definition of Toso cell surface receptors are portions of Toso cell surface receptors; that is, either the fill-length receptor may be used, or functional portions thereof. In a preferred embodiment, the extracellular domain of Toso may be used without or without the transmembrane region. In an additional preferred embodiment, the cytoplasmic domain of Toso may be used without or without the transmembrane region. In addition, the assays described herein may utilize either isolated Toso receptors (including both soluble and membrane or lipid bound receptors) or cells comprising the Toso receptors, with the latter being preferred.

Generally, in a preferred embodiment of the methods herein, the Toso cell surface receptor or the candidate agent is non-diffusably bound to an insoluble support having isolated sample receiving areas (e.g., a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block the apoptosis-modulating sequence when the Toso protein is bound to the support), direct binding to "sticky" or ionic supports, chemical crosslinking, the synthesis of the Toso protein or receptor on the surface, etc. Following binding of the Toso protein or receptor, excess unbound material is removed by washing. The sample receiving areas may then be blocked through incubation with bovine serum albumin (BSA), casein or other innocuous protein or other moiety.

A candidate bioactive agent is added to the assay. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein—protein binding assays, electrophoretic mobility shift assays, immunoassays for protein binding, functional assays (phosphorylation assays, etc.) and the like.

The term "candidate bioactive agent" or "exogeneous compound" as used herein describes any molecule, e.g., protein, oligopeptide, small organic molecule, polysaccharide, polynucleotide, etc., with the capability of directly or indirectly modulating apoptosis, which can be in response to ligand binding or in the absence of ligand binding. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occuring proteins or fragments of naturally occuring proteins. Thus, for example, cellular extracts containing proteins, or random or directed digests of proteinaceous cellular extracts, may be used. In this way libraries of procaryotic and eucaryotic proteins may be made for screening against Toso. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occuring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem. 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et at., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occuring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occuring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

The determination of the binding of the candidate bioactive agent to the Toso receptor may be done in a number of ways. In a preferred embodiment, the candidate bioactive agent is labelled, and binding determined directly. For example, this may be done by attaching all or a portion of the Toso cell-surface receptor to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g., radioisotope, fluorescers, enzyme, antibodies, particles such as magnetic particles, chemiluminescers, or specific binding molecules, etc. Specific binding molecules include pairs, such as biotin and streptavidin, digoxin and antidigoxin, etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the receptors (or proteinaceous candidate agents) may be labeled at tyrosine positions using $^{125}$I, or with fluorophores. Alternatively, more than one component may be labeled with different labels; using $^{125}$I for the receptors, for example, and a fluorophor for the candidate agents.

In a preferred embodiment, the binding of the candidate bioactive agent is determined through the use of competitive binding assays. In this embodiment, the competitor is a binding moiety known to bind to the target molecule, such as an antibody, peptide, binding partner, ligand, etc. Under certain circumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the receptor for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the Toso receptor and thus is capable of binding to, and potentially modulating, the activity of the Toso receptor. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the Toso receptor with a higher affinity. Thus, if the candidate bioactive agent is labeled, the presence of the label on the support, coupled with a lack of competitor binding, may indicate that the candidate agent is capable of binding to the Toso receptor.

In a preferred embodiment, the methods comprise differential screening to identity bioactive agents that are capable of modulating the activitity of the Toso receptors. In this embodiment, the methods comprise combining a Toso cell surface receptor and a competitor in a first sample. A second sample comprises a candidate bioactive agent, a cell surface Toso receptor and a competitor. The binding of the competitor is determined for both samples, and a change, or difference in binding between the two samples indicates the presence of an agent capable of binding to the Toso receptor and potentially modulating its activity. That is, if the binding of the competitor is different in the second sample relative to the first sample, the agent is capable of binding to the Toso receptor. Alternatively, a preferred embodiment utilizes differential screening to identify drug candidates that bind to the native Toso receptor, but cannot bind to modified receptors. The structure of the Toso receptor may be modeled, and used in rational drug design to synthesize agents that interact with that site. Drug candidates that modulate apoptosis are also identified by screening drugs for the ability to either enhance or reduce the apoptotic response which is triggered by binding to the Toso receptor.

Positive controls and negative controls may be used in the assays. Preferably all control and test samples are performed in at least triplicate to obtain statistically significant results. Incubation of all samples is for a time sufficient for the binding of the agent to the Toso receptor. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein—protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of Toso may also be done. In a preferred embodiment, methods for screening for a bioactive agent capable of modulating the activity of Toso comprise the steps of adding a candidate bioactive agent to a sample of Toso, as above, and determining an alteration in the biological activity of Toso. "Modulating the activity of Toso" includes an increase in activity, a decrease in activity, or a change in the type or kind of activity present. Thus, in this embodiment, the candidate agent should both bind to Toso (although this may not be necessary), and alter its biological or biochemical activity, as defined herein. The methods include both in vitro screening methods, as are generally outlined above, and in vivo screening of cells for alterations in the presence, distribution, activity or amount of Toso.

Thus, in this embodiment, the methods comprise combining a Toso sample and a candidate bioactive agent, and testing the Toso biological activity as is known in the art to evaluate the effect of the agent on the activity of Toso. By "Toso activity" or grammatical equivalents herein is meant the ability of Toso after activation to modulate apoptosis. As outlined herein, upon T cell activation, Toso is activated, initiating a signalling pathway that results in modulation of apoptosis. Such modulation may result in response to either of the extracellular or cytoplasmic domains of Toso and may correspond to a decrease or an increase in apoptosis. In a preferred embodiment, the activity of the extracellular or cytoplasmic domain of Toso is increased; in another preferred embodiment, the activity of the extracellular or cytoplasmic domain of Toso is decreased. Thus, bioactive agents that are antagonists (i.e. decrease the activity of Toso proteins) are preferred in some embodiments, and bioactive agents that are agonists (i.e., increase the activity of Toso proteins) may be preferred in other embodiments. For example, agents which bind to a Toso receptor, but do not allow activation or signalling of the receptors could be antagonists. In addition, agents which bind to a Toso receptor, may increase activation or signalling of the receptors, and thus act as agonists.

In a preferred embodiment, the invention provides methods for screening for bioactive agents capable of modulating the activity of a Toso cell-surface receptor. The methods comprise adding a candidate bioactive agent, as defined above, to a cell comprising Toso cell-surface receptors or the Toso cytoplasmic domain. Preferred cell types include, but are not limited to mammalian cells, for example T cells such as Jurkat cells, 293 or 31 cells. The cells contain a recombinant nucleic acid that encodes a Toso receptor; that is, the cells express Toso either at the surface of the cell or within the cell. In a preferred embodiment, a library of candidate agents are tested on a plurality of cells.

The cells are then exposed to an apoptotic agent that will induce apoptosis in control cells, i.e., cells of the same type but that do not contain the exogeneous nucleic acid encoding Toso. Suitable apoptotic agents include, but are not limited to, Fas-mediated apoptosis inducers, including the Fas ligand (FasL) and anti-Fas receptor antibodies (particularly monoclonal antibodies), chemotherapeutic agents, for example, cisplatin, taxol, methotrexate, etc.; tumor necrosis factor-alpha (TNF-α); FADD, PMA; ionomycin; and staurosporine.

The effect of the candidate agent on apoptosis is then evaluated. If Toso is acting, i.e., there is no antagonistic agent present, the cells will not undergo programmed cell death. However, if antagonistic agents are present, the cells will undergo apoptosis.

Detection of apoptosis may be done as will be appreciated by those in the art. In one embodiment, annexin is used. Annexin will stain cells undergoing apoptosis. Accordingly, annexin can be used as an affinity ligand, and attached to a solid support such as a bead, a surface, etc. and used to pull out apoptotic cells. Similarly, annexin can Lb be used as the basis of a fluorescent-activated cell sorting (FACS) separation. Apoptosis may also be detected by staining of cells with propidium iodide, by use of mitochondrial dyes, or by use of FRET constructs.

In this way, bioactive agents are identified. Compounds with pharmacological activity are able to enhance or interfere with the activity of the Toso receptor. The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like.

Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Without being bound by theory, it appears that Toso is an important signalling step in apoptosis. Accordingly, disorders based on mutant or variant Toso genes may be determined. In one embodiment, the invention provides methods for identifying cells containing variant Toso genes comprising determining all or part of the sequence of at least one endogenous Toso genes in a cell. As will be appreciated by those in the art, this may be done using any number of sequencing techniques. In a preferred embodiment, the invention provides methods of identifying the Toso genotype of an individual comprising determining all or part of the sequence of at least one Toso gene of the individual. This is generally done in at least one tissue of the individual, and may include the evaluation of a number of tissues or different samples of the same tissue. For example, putatively cancerous tissue of an individual or any diseased tissue are preferred samples. The method may include comparing the sequence of the sequenced Toso gene to a known Toso gene, i.e., a wild-type gene.

The sequence of all or part of the Toso gene can then be compared to the sequence of a known Toso gene to determine if any differences exist. This can be done using any number of known homology programs, such as Bestfit, etc. In a preferred embodiment, the presence of a a difference in the sequence between the Toso gene of the patient and the known Toso gene is indicative of a disease state or a propensity for a disease state, as outlined herein.

The present discovery relating to the role of Toso in apoptosis thus provides methods for inducing apoptosis in cells. In a preferred embodiment, the Toso proteins, and particularly Toso fragments, are useful in the study or treatment of conditions which are mediated by apoptosis, i.e. to diagnose, treat or prevent apoptosis-mediated disorders. Thus, "apoptosis mediated disorders" or "disease state" include conditions involving immune disorders or cellular processes mediated by apoptosis, as well as conditions which have inappropriate apoptosis or a lack thereof. Accordingly, apoptosis mediated disorders include, but are not limited to, any disease characterized by lymphoid or T cell overactivity, including, but not limited to Sjogrens, mixed connective tissue disease, autoimmune disorders including, but not limited to, lupus (SLE), rheumatoid arthritis (RA), multiple sclerosis, and autoimmune diseases which are tissue specific, for example liver (hepatitis), kidney (nephritis) or Hashimotois (thyroiditis); diseases where T cells actively destroy cells, for example, cytotoxic effects including, but not limited to, transplant rejection, disease conditions based on graft vs. host or host vs. graft reactions; conditions where cells of any kind that are not dying express Toso appropriately, for example, cancer of T or B cell origin (where increased apoptosis would be desirable), including but not limited to, leukemias and lymphomas, or Chrohn's disease, skin inflammatory disorders (psoriasis, eczema); and diseases secondary to altered immunoglobulin production such as Waldenstroms, and multiple myeloma.

Thus, in one embodiment, methods of modulating apoptosis in cells or organisms are provided. In one embodiment, the methods comprise administering to a cell an anti-Toso antibody that reduces or eliminates the biological activity of the endogenous Toso receptor. Alternatively, the methods comprise administering to a cell or organism a recombinant nucleic acid encoding a Toso receptor. As will be appreciated by those in the art, this may be accomplished in any number of ways. In a preferred embodiment, the activity of Toso is increased by increasing the amount of Toso in the cell, for example by overexpressing the endogenous Toso or by administering a gene encoding Toso, using known gene-therapy techniques, for example. In a preferred embodiment, the gene therapy techniques include the incorporation of the exogeneous gene using enhanced homologous recombination (EHR), for example as described in PCT/US93/03868, hereby incorporated by reference in its entireity.

In one embodiment, the invention provides methods for diagnosing an apoptosis related condition in an individual. The methods comprise measuring the activity and expression of Toso in a tissue from the individual or patient, which may include a measurement of the amount or specific activity of Toso. This activity is quantified and compared to the activity of Toso from either an unaffected second individual or from an unaffected tissue from the first individual. When these activities are different, the first individual may be at risk for an apoptosis mediated disorder. In this way, for example, monitoring of immunosuppression may be done, by monitoring the levels of Toso. Similarly, Toso levels may correlate to levels of T cell activity or levels of immune responsiveness.

In one embodiment, the Toso proteins of the present invention may be used to generate poyclonal and monoclonal antibodies to the extracellular or cytoplasmic domains of Toso proteins, which are useful as described herein. Similarly, the Toso proteins can be coupled, using standard technology, to affinity chromatography columns. These columns may then be used to purify Toso antibodies. In a preferred embodiment, the antibodies are generated to epitopes unique to the Toso protein; that is, the antibodies show little or no cross-reactivity to other proteins. These antibodies find use in a number of applications. For example, the Toso antibodies may be coupled to standard affinity chromatography columns and used to purify Toso proteins. The antibodies may also be used as blocking polypeptides, as outlined above, since they will specifically bind to the Toso protein.

In one embodiment, a therapeutically effective dose of a Toso is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for Toso degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the Toso proteins of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the Toso may be directly applied as a solution or spray.

The pharmaceutical compositions of the present invention comprise a Toso protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropyl amine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLE 1

Molecular Cloning and Chromosomal Localization of Toso.

Jurkat cells (human T cell line) were infected with a retroviral Jurkat T cell cDNA library to screen for cDNAs that encode inhibitory molecules for Fas-induced apoptosis. A retroviral library containing $2 \times 10^6$ independent cDNA inserts was constructed from Jurkat cell mRNA by standard methods (Kinoshita and Nolan, unpublished) using a retrovirus vector pBabeMN (Kinoshita, et al. (1997)). The library was transfected into an ecotropic virus packaging cell line, φNX-Ampho, as described previously. Jurkat cells were spin-infected with the supernatant from φNX-A cells resulting in 20–40% infection using this method as determined by doping of the library with a marker retrovirus pBabeMN-LacZ or pBabeMN-Lyt-2-α (194 amino acids), which does not have cytoplasmic domain (Tagawa, et al., *Proc. Natl. Acad. Sci.* 83:3422–3426 (1986)). Jurkat cells were aliquoted into 96-well plates in media containing 10 ng/ml of anti-human Fas mAb, CH11, (Kamiya Biomedical Company, CA 91359, U.S.A.) for 15 days. Jurkat cells, under conditions empirically derived, were sensitive to Fas-mediated apoptosis with a spontaneous survival rate under our conditions of 2–3 per $10^6$ cells. Cells that survived the Fas-mediated killing were identified by outgrowth in the 96 well plate format, expanded, total RNA extracted, and cDNA inserts rescued using RT-PCR (AMV reverse transcriptase from Promega, Wis. 53711, U.S.A. and Vent DNA polymerase from New England Biolabs, Inc., MA 01915, U.S.A.) with primers 5'-GCT CAC TTA CAG GCT CTC TA (LibS, SEQ ID NO:22) and 5'-CAG GTG GGG TCT TTC ATT CC (LibA; SEQ ID NO:23), which were located 282 bp and 56 bp nucleotides upstream and downstream of cDNA insert cloning sites. After an initial denaturation at 94° C. for 5 minutes, each cycle of amplification consisted of 30 second denaturation at 94° C., followed by a 30 second-annealing at 58° C. and 2 minutes extension at 72° C. After 35 cycles, the final product was extended for 10 minutes at 72° C. The rescued inserts were digested with BamHI-SalI (Promega) or BstXI (Promega), and ligated into the pBabeMN retrovirus vector. The cloned retrovirus containing the novel insert was infected into Jurkat cells. Cells were cultured with 10 ng/ml anti-Fas mAb to confirm whether the inhibitory effect was caused by cDNA inserts of retrovirus. 26 clones were obtained that were resistant to Fas-induced apoptosis, of which 12 carried cDNA inserts. After a second round of anti-Fas screening, one clone, termed here Toso, demonstrated potent inhibition of Fas-induced apoptotic signaling.

The cDNA insert of Toso was found to contain a 5'-non-coding region of 73 nucleotides, a coding region of 1173 nucleotides (390 amino acids) and a 3'-non-coding region of 665 nucleotides. (See FIG. 1, SEQ ID NO:1). The ATG initiation codon is contained within a standard Kozak consensus sequence. Kyte-Doolittle hydropathy plot analysis showed that Toso has two hydrophobic regions: the amino-terminal residues from 1 to 17 correspond to the deduced signal sequence (underlined) and residues from 254 to 272 (double underlined) correspond to a presumptive transmembrane region [Hofmann and Stoffel, f993, analysis was performed using DNAsis-Mac V2.0 (Hitachi Software Engineering, Co. Ltd., Japan)], suggesting that Toso is a type 1 integral membrane protein. (See FIG. 2b). The predicted molecular weight of Toso is 41 kDa. The cytoplasmic region of Toso has a basic amino acid-rich region (from $R^{274}$ to $R^{323}$), a proline-rich region (from $p^{334}$ to $p^{346}$), and an acidic amino acid-rich region (from $E^{378}$ to $D^{384}$) (See FIGS. 2a and 2b, SEQ ID NO:2). BLAST search analysis revealed that Toso is a unique gene (Altschul, et al., (1990)). The extracellular domain of Toso has homology to the immunoglobulin variable (IgV) domains, which is characterized by motifs in the β-strand B, D and F regions, (residues VTLTC (SEQ ID NO:24), RV (or F or I) and DSG (or A)-Y-CA (SEQ ID NO:25)) (Williams and Barclay, Ann. Rev. Immunol., 6:381–405 (1988)). Importantly, the cysteines in the IgV-like motif VTIKC (SEQ ID NO:26) at position 33 in Toso, as well as the cysteine in the IgV-like motif DSGVYAC (SEQ ID NO:27) at position 98, are appropriately distanced as in other IgV-like domains to form a disulphide bond. Toso also contains within the Ig domains two additional cysteines that are not conserved in other IgV-like domains. Thus, the presumptive extracellular domain has all the requisite features that demarcate it as a potential IgV-like domain. The cytoplasmic region of Toso has partial homology to FAST kinase, acid sphingomyelinase, insulin receptor substrate-1 (IRS-1) and the apoptosis inhibitor from Orgyia pseudotsugata nuclear polyhedrosis virus (Op-1AP) (FIG. 3), which might function to initiate some of the signaling systems acted upon by Toso.

Poly(A)' RNA was prepared from Jurkat cells stimulated for 24 hours with 10 ng/ml PMA (SIGMA) and 500 ng/ml lonomycin (SIGMA). The first strand of cDNA was synthesized with 10 μg Poly (A) RNA using oligo-dT primers and performed PCR with primers, 5'-AGA ATT CTC TCT AGG GGC TCT TGG ATG (SEQ ID NO:28: See FIG. 1 (SEQ ID NO:1) where the EcORI site is underlined) and 5'-ATA AAG CTT CTC AGG GCA CAG ATA GAT GG (SEQ ID NO:29, Hind III site is underlined), which were located 23 bp and 136 bp nucleotides upstream and downstream of the Toso coding region, respectively. The 1.3 kbp fragment was ligated into pBluescript SK(+). Five independent clones were picked up and sequenced using cycle sequencing ready reaction kit (Perkin Elmer). The deduced amino-acid sequences from the five independent clones were completely identical to the gene from the cDNA library screening, although two silent mutations were found within the original gene as compared to the PCR consensus sequences.

The Toso gene was mapped to a human chromosome by using a panel of 17 human X Chinese hamster hybrid cell lines derived from several independent fusion experiments (Francke et al., 1986). PCR primers used to amplify Toso sequence derived from the 3' untranslated region were 5'-AGA GGC ATA GCT ATT GTC TCG G (SEQ ID NO:30, sense, located 369 bp downstream of the coding region), and 5'-ACA TTT GGA TCA GGG CAA AG (SEQ ID NO:31, anti-sense, 508 bp downstream of the coding region). The size of the PCR product was 159 bp. The PCR conditions were 94° C., 90 seconds; then 35 cycles of 94° C., 20 seconds, 55° C., 30 seconds, 72° C. 45 seconds, followed by 72° C., 5 minutes. Specific PCR products were obtained from human genomic DNA, and hybrid cell lines that carry human chromosome 1. The PCR product was sequenced to confirm its identity.

To map the Toso gene locus more precisely, two human radiation hybrid (RH) mapping panels were typed by PCR. GeneBridge 4 (Whitehead Institute/MIT Genome Center) and Stanford G3 (Stanford Human Genome Center), were obtained from Research Genetics, Inc. (Cox, et al., Science, 250:245–250 (1990); Walter, et al., Net Genet, 7:22–28 (1994)), and samples were typed using the primers and PCR conditions described above. Results of the maximum likelihood analysis (Boehnke, et al., Am. J. Hum. Genet., 49:1174–1188 (1991)) were obtained by submitting the raw scores to: http://www-genome.wi.mit.edu/cgibin/contig/ rhmapper.pl and http://wwwshge.stanford.edu/rhserver2/ rhscrver_form.html. The cytological localization of the Toso gene was deduced from the cytogenetic information about the flanking markers in Bray-Ward et al (Bray-Ward, et al., Genomics, 32:1–14 (1996)). In the Stanford G3 mapping panel, Toso cosegregated with chromosome 1 marker D1 S3553 on all 83 Stanford G3 panel RH cell lines. D1 S3553 is a known marker of chromosome 1 bin 115 on the SHGC RH map. In the GeneBridge 4 mapping panel, Toso is located 5.4 $cR_{3000}$ and 1.7 $cR_{3000}$ from D1 S504 and WI-9641, respectively. The order of loci in this region from centromere to qter is: D1S412-D1S306 D1S504-Toso-WI-9641-D1S491-D1S237. According to Bray-Ward et al. (1996), the YACs containing the more proximal markers D1S412 (bin 104), D1S477 (bin 109) and D1S504 (bin 114) were mapped to 1q25–q32, 1q31–q32 and 1q25–q32 respectively, and the YACs containing the more distal markers D1 S491 (bin 118), D1 S414 (bin 121) and D1 S237 (bin 124) were mapped to essentially the same region, 1q3132, 1q31–q32 and 1q32–q41, respectively. Thus, the Toso gene is located at 1 q31–q32, a region in which several chromosomal abnormalities relating to leukemias are localized.

Toso is a negative regulator of Fas-mediated cell death in lymphoid cells, and may therefore be involved in oncogenic events or resistance to chemotherapy (Friesen, et al., *Nature Medicine.* 2:574–577 (1996)). The gene for Toso localizes within human chromosome region 1q31–q32. Chromosomal changes in 1q32 are frequently observed in human cancer, including various types of hematopoietic malignancies and solid tumors (Jinnai, et al., *Am. J. Hematol,* 35:118–124 (1990); Mertens, et al., *Cancer Res.,* 57:2765–2780 (1997); Mitelman, et al., *Nat. Genet.,* 417–474 (1997); Schmid and Kohler, *Cancer Genet. Cytogenet,* 11:121–23 (1984); Shah, et al., *Cancer Genet. Cytogenet,* 61:183–192 (1992); Waghray, et al., *Cancer Genet. Cytogenet,* 23:225–237 (1986); Yip, et al., *Cancer Genet. Cytogenet,* 51:235–238 (1991)). Furthermore, studies in nude mice demonstrated that duplication of the chromosome segment of 1 q11–q32 is associated with proliferation and metastasis of human chronic lymphocytic leukemic B-cells (Ghose, et al., *Cancer Res.,* 50:3737–3742 (1990)), suggesting the presence of dominantly acting growth regulatory or cell survival genes. Thus, Toso is a candidate for evaluation as a proto-oncogene in several proliferative and metastatic neoplasms.

EXAMPLE 2

Toso Inhibits Fas-, TNFα- and FADD-Induced Apoptosis.

Jurkat cells that express the receptor for ecotropic murine retroviruses ("Jurkat.ecoR") were infected with retroviruses that express Toso and control vectors, pBabeMN-Toso, pBabeMN-lacZ and pBabeMN-Lyt-2-α'(α' form of mouse CD8α chain) (Tagawa, et al. (1986)). Jurkat.ecOR cells were infected with pBabeMN-lacZ, pBabeMN-Lyt-2-α', and pBabeMN-Toso. At 72 hours postinfection, infection frequency of pBabeMN-lacZ and pBabeMN-Lyt-2α' were determined to be 45% and 58%, respectively. Jurkat cells were then cultured with 10 ng/ml anti-Fas mAb for 24 hours. After 12 or 24 hours, the cells were stained with 100 μg/ml ethidium bromide (SIGMA) and 100 μg/ml acridine orange (SIGMA). Apoptotic cells and non-apoptotic cells were identified with UV microscopy as described (MacGahon, et al., *The End of the (Cell) Line: Methods for the Study of Apoptosis in vitro,* in Methods in cell biology, L. J. Schwartz and B. A. Osborne, eds., San Diego, Calif., Academic Press, Inc., pp. 172–173 (1995)).

Jurkat.ecOR cells expressing Toso were resistant to apoptosis induced by 10 ng/ml of anti-Fas mAb, whereas Jurkat cells, Jurkat.ecOR cells and Jurkat.ecOR cells that expressed lacZ or Lyt-2-α', all succumbed to apoptotic death (FIG. 4a).

Staurosporine is a bacterial alkaloid that is a broad spectrum inhibitor of protein kineses (Tamaoki and Nakano, *Biotechnology,* 8:732–735 (1990)) and induces programmed cell death in various cell lines and dissociated primary cells in culture (Ishizaki, et al, *J. Cell Biol.,* 121:899–908 (1993); Jacobson, et al., *Nature,* 361:365–369 (1993); Raff, et al., *Science.* 262:695–700 (1993)). Ceramide generation is implicated in a signal transduction pathway that mediates programmed cell death induced by Fas and TNF-α (Cifone, et al., *J. Exp. Med.,* 180:1547–1552 (1994); Obeid, et al., *Science,* 259:1769–1771 (1993)). pBabeMN-LacZ infected cells were counted by microscopic observation; infection frequency was determined to be 57%. At 72 hours postinfection, Jurkat.ecOR cells and Jurkat.ecOR cells infected with pBabeMN-lacZ and pBabeMN-Toso were cultured with anti-Fas mAb, staurosporine and ceramide for 24 hours. Although Jurkat.ecOR cells expressing Toso were resistant to Fas-mediated apoptosis over a range of antiFas dilutions, these cells were not resistant to any concentration of staurosporine- or ceramide-induced apoptosis (FIG. 4b).

The Fas receptor has homology to the TNF-α receptor, and these two receptors share analogous signaling systems as well as several intracellular mediators (Hsu, et al., *Cell,* 84:299–308 (1996)). The protective effect of Toso against TNF-α-induced apoptosis was tested by culturing Jurkat.ecOR cells expressing Lyt-2-α' or Toso with 10 ng/ml of anti-Fas mAb or 1 μg/ml of TNF-α in the presence of 0.1 μg/ml of cyclohexamide (CHX) for 12 hours and apoptotic cells were counted. The infection frequency of pBabeMN-Lyt-2-α' was determined to be 58%. Toso inhibited Fas induced apoptosis in the presence of CHX and also protected against TNF-α-induced apoptosis in comparison to Jurkat.ecoR expressing Lyt-2-α' (FIG. 4d). Thus the TNF-α and Fas signaling pathways may converge at a common point that can be inhibited by Toso.

Fas-mediated apoptosis is activated through FADD. For FADD-induced apoptosis, mouse FADD (a gift from Dr. Angeles Estelles, Dept. Mol. Pharm., Stanford Univ.) was ligated into pBabeMN retroviral vector. Jurkat.ecoR cells expressing Lyt-2-α' or Toso were infected with pBabeMN-LacZ or pBabeMN-FADD. After 24 hours infection with FADD, the cells were stained with ethidium bromide and acridine orange and counted the apoptotic cells. The effect of Toso on FADD-induced apoptosis was investigated by infecting Jurkat.ecoR cells expressing Lyt-2-α' or Toso, with pBabeMN-LacZ or pBabeMN-FADD. The reinfection efficiency was approximately 40% using pBabeMN-LacZ. Jurkat.ecoR cells were infected with pBabeMN-Lyt-2-α' and pBabeMN-Toso. Infection frequency of pBabeMN-Lyt-2-α' was determined to be 72%. Jurkat.ecoR cells expressing Lyt-2-α' or Toso were infected with pBabeMNLacZ or pBabeMN-FADD and apoptotic cells were counted at 24 hourrs postinfection. Infection frequency of pBabeMN-lacZ in Jurkat.ecoR cells expressing Lyt-2-α' and Toso was determined to be 39% and 43%, respectively. As shown in FIG. 4c, FADD induced apoptosis in 45% of control Jurkat cells. However, FADD failed to induce apoptosis in Jurkat.ecoR cells constitutively expressing Toso. The results also suggest that Toso's effect is not due to down regulation of FADD gene expression.

The downstream effects of Toso on known inhibitors of apoptosis, were evaluated by western blot analysis of Bcl-2 and BCl XL expression levels in Toso expressing cells. Bcl-2 overexpression can block Fas-induced apoptosis as well as staurosporine-induced apoptosis (data not shown). No change in the levels of expression of Bcl-2 or BcI XL was observed by Western blot (data not shown). Thus, it appears that intracellular signaling events generated by FADD can be directly and efficiently blocked by signals emanating from Toso at a point prior to engagement of Bcl-2 and Bcl XL.

The effect of overexpression of Toso on processing of caspase-8, which associates with FADD, was evaluated. The processed form (p20) of FLICE after Fas activation was greatly reduced in pBabeMN-Toso-infected Jurkat.ecoR cells in comparison with control Jurkat.ecoR cells (see FIG. 5a). To detect caspase-8, whole-cell lysates ($2 \times 10^6$ cells per lane) were resolved by SDS-PAGE, transferred to an membrane and processed with goat anti-Mch5 p20 antibody (Santa Cruz Biotechnology, Inc., Santa Cruz, Calif. 95060, U.S.A.) as described above. This data indicates that Toso inhibits caspase-8 processing after Fas activation.

Recently several groups have reported cFLIP is a caspase-8 inhibitor. We performed semi-quantitative RT-PCR to detect cFLIP mRNA expression. To detect cFLIP mRNA expression, a 1.1 kbp fragment (998–2061) of the cFLIP gene (U97074) was amplified with primers 5'-GGG AGA AGT AAA GAA CAA AG (SEQ ID NO:32) and 5'-CGT AGG CAC AAT CAC AGC AT (SEQ ID NO:33) for 35 cycles as described above. The sequence of the 1.1 kbp PCR product was verified using cycle sequencing ready reaction kit (Perkin Elmer, Calif. 94404, U.S.A.). As a control, β-actin cDNA was amplified for 15 and 25 cycles as described above. cFLIP expression was induced by Toso (FIG. 5b). These results strongly suggest that the extracellular domain of Toso inhibits Fas-induced apoptosis by preventing caspase-8 processing through cFLIP upregulation.

Toso did not inhibit staurosporine-induced programmed cell death and staurosporine has been shown to activate caspase-8 (Jacobsen, et al., *J. Cell Biol.*, 133:1041–1051 (1996)). Therefore, additional Toso effects do not occur downstream, nor at the level, of caspase-8. Supporting this, Toso also did not inhibit ceramide-induced apoptosis, which acts downstream or independent of caspase-8 as demonstrated in experiments using the caspase-8-specific inhibitor peptide, DEVD-CHO (Gamen, et al., *FEBS Lett.*, 390:232–237 (1996)), which does not inhibit ceramide-induced apoptosis. Overexpression of Bcl-2 or Bcl-XL is known to prevent apoptosis in response to ceramide and staurosporine (Geley, et al., *FEBS Lett.*, 400:15–18 (1997); Susin, et al., *J. Exp. Med.*, 186:25–37 (1997); Takayama, et al., *Cell*, 80:279–284 (1995); Zhang, et al., *Proc. Natl. Acad. Sci. USA*, 93:5325–5328 (1996)). Toso did not change the expression levels of Bcl-2 nor Bcl-XL in Jurkat cells, showing that neither Bcl-2 nor Bcl-XL were involved in the protective activities of Toso. Taken together then, Toso activates an inhibitory pathway that prevents caspase-8 activation following Fas stimulation through upregulation of cFLIP, and not by blocking apoptotic signals downstream or at the level of caspase-8. This explains the apparent specificity of the blockade to TNF family-related surface receptors that use caspase-8 for apoptotic signaling.

Cells expressing Toso alone were mixed with an equal number of cells expressing lacZ. After one round of Fas stimulation, no lacZ-expressing cells remained as assayed by X-gal. In addition, Jurkat.ecoR cells were infected with pBabeMN-Toso-IRES-GFP. After infection, cells were cultured with (α-Fas (+)) or without (α-Fas (−)) 50 ng/ml of anti-Fas mAb. In the absence of anti-Fas mAb treatment (Fas (−))., 46% GFP negative cells and 54% GFP positive cells were observed in pBabeMN-Toso-IRES-GFP-infected Jurkat.ecoR cells. After five days culture with anti-Fas mAb, survivors were obtained from pBabeMN-Toso-IRES-GFP-infected Jurkat.ecoR cells, but not from control pBabeMN-IRES-GFP-infected Jurkat.ecoR cells (data not shown); 99.7% of surviving Jurkat cells expressed GFP as shown in FIG. 4e (Fas(+)). These data indicate that cells that express the extracellular domain of Toso are protected from Fas-induced apoptosis and suggests that Toso does not exert its effect as a secreted form.

EXAMPLE 3
The Immunoglobulin Domain and the Transmembrane Region of Toso Are Required for Inhibition of Fas-induced Apoptosis.

The C-terminus deletion mutants (TosoΔ(377–390).HA, TosoΔ(334–390).HA, TosoΔ(281–390).HA and TosoA(252–390).HA), the N-terminus deletion mutant (TosoΔ(29–187).HA) and the fusion protein (Lyt-2/Toso(271–390).HA) of the extracellular domain and transmembrane region from Lyt-2-α' and the cytoplasmic domain from Toso, which have the influenza virus hemmagglutinin tag (HA) in C-terminus, were generated by. Primers in the antisense orientation, carrying the 20 nucleotide sequences of Toso located upstream of the deletion sites, HA tag sequence and an in-frame termination codon, as well as NcoI site, were synthesized. The DNA fragment of the Toso gene from the XhoI site located in the extracellular domain to the Nco1 site that is located in 3' non-coding region was replaced with the PCR products amplified from pBabeMN-Toso using LibS and each primer described above. A primer for TosoΔ(29–187).HA in the antisense orientation carrying the 20 nucleotides located after the leader peptides of Toso and XhoI site was synthesized. The DNA fragment from DraIII site, which is located 190 bp upstream of cDNA insert cloning sites, to XhoI site in pBabeMN-Toso.HA was replaced with the PCR product amplified from pBabeMN-Toso using LibS and the primer. For Lyt2/Toso(271–390) .HA, primer in sense orientation which is carried a BamHI site and the 20 nucleotides located upstream of the cytoplasmic domain was synthesized. The DNA fragment from Bcl I site, which is located in the end of transmembrane region of Lyt-2-α', to SalI site, which is located downstream of Lyt-2-α' cloning sites in pBabeMN-Lyt-2-α', was replaced with the PCR product amplified from pBabeMN-Toso.HA using LibA and the primer. All mutants generated by PCR were verified by DNA sequencing using cycle sequencing ready reaction kit. Toso deletion mutants prepared as described above were epitope-tagged in order to delineate the regions responsible for anti-apoptotic signal transduction, (FIGS. 6a and 6b). Toso.HA (fused to the hemagglutinin, HA, tag) had an apparent molecular weight of 60 kDa, suggesting Toso is heavily glycosylated. The cell surface expression of Fas using anti-human Fas mAb, CH11, was determined by FACS to explore whether Toso has an effect on Fas expression. Fas was expressed at similar levels on the surface of cells expressing either full-length Toso, Toso deletion mutants, or control vector. Thus, the extracellular domain of Toso neither downregulates Fas, nor directly interferes with the ability of the antibody to bind and presumably stimulate Fas.

Jurkat.ecOR cells were infected with pBabeMN-Lyt-2-α'.HA, pBabeMN-Toso. HA, pBabeMN-TosoΔ(377–390).HA, pBabeMN-TosoΔ(334–390). HA, pBabeMN-TosoΔ(281–390).HA, pBabeMNToso Δ(252–390).HA and pBabeMN-TosoΔ(29–187).HA. Jurkat cells were cultured with 10 ng/ml anti-Fas mAb for 24 hours and apoptotic cells were counted. Apoptosis was readily induced in control Jurkat.ecoR cells and Jurkat.ecoR cells expressing Lyt-2-α'.HA, whereas apoptosis was markedly inhibited in Jurkat.ecoR cells that expressed Toso.HA (FIG. 6a). Deletions of regions of the cytoplasmic domain of Toso from 334 to 390 still inhibited apoptosis. Moreover, a deletion of Toso lacking the entire cytoplasmic domain still retained substantial anti-apoptotic ability. Thus, the cytoplasmic domain of Toso is not absolutely required for the anti-apoptotic effects on Fas antibody-stimulated cells. (See Example 5, below) These results indicate that the homologies observed in the cytoplasmic region of Toso, as shown in FIG. 3, are not the only sources of the anti-apoptotic signals generated by a Toso complex, although the cytoplasmic regions are required for enhancing the anti-apoptotic effects of Toso.

The Toso mutant lacking the transmembrane and cytoplasmic domains demonstrated that inhibition of Fas-induced apoptosis by Toso requires its insertion into membranes. As shown in FIG. 6a, soluble TosoΔ(252–390).HA afforded no protection from apoptosis. Expression of the TosoΔ(252–390).HA protein was confirmed by western blot analysis of culture supernatants. Supernatants derived from pBabeMN-TosoΔ(252–390). HA-transfected 293T cells did not inhibit Fas-induced apoptosis, indicating that a membrane-proximal event dependent on cis—localization of Toso is required for blockade of the Fas-mediated death signal.

Many cell surface receptor complexes act through oligomerization and most immunoglobulin (Ig) domain proteins exist in homodimeric and heterodimeric Ig forms, functioning as self-assembling systems. Disruption of the Ig domain of Toso completely abrogated the anti-apoptotic ability of Toso (TosoΔ(29–187).HA). (See FIG. 6a). Further, a chimeric Lyt-2Toso fusion protein in which the cytoplasmic domain of Toso was coupled to the extracellular and transmembrane region of Lyt-2-α' (α' form of murine CD8α, which forms homodimers at the cell surface) (Tagawa, et al., (1986)) failed to inhibit Fas-induced apoptosis. Furthermore, anti-mouse CD8a mAb (Lyt-2) was used to crosslink the Lyt-2-Toso chimeras and induce multimerization of the Toso cytoplasmic domains. These results suggest that some form of Ig domain mediated dimerization of Toso is required to initiate the anti-apoptotic effect in conjunction with the cytoplasmic region of Toso or other cell surface Toso-associating proteins. Toso.HA-expressing Jurkat.ecoR cells ($5 \times 10^6$ cells) were incubated with 2 mM BS3 (PIERCE, Rockford, Ill. 61105, U.S.A.) for 1 hour at 4° C. After incubation, 1 M Tris-HCI was added to a final concentration of 10 mM and cells were incubated for 15 minutes at 4° C. Whole-cell lysates were resolved by SDS PAGE, transferred to a membrane and processed with mouse monoclonal antihemagglutinin antibody (HA.11) (Babco) as described above. Apparent crosslinking molecular complexes at 150, 240, 300 kDa were detected (See FIG. 6c). This result first indicates that Toso is a surface expressed receptor. The results are consistent with an association of Toso with another surface protein(s) of molecular weight 90 kDa. The several molecular weights observed for the crosslinked complexes are also minimally consistent with stochiometric mixtures of 60 and 90 kDa molecules.

Deletion analysis of Toso indicated that surface expression of the immunoglobulin V-like region is necessary to inhibit Fas-induced-apoptosis and that the cytoplasmic domain of Toso is insufficient and indeed partly expendable for the anti-apoptotic function. Deletion of the cytoplasmic domain resulted in abrogation of only about half of the anti-apoptotic effect. This suggests that Toso must be expressed at the cell surface in a manner where it presumably interacts other surface molecule(s) that propagate an anti-apoptotic signal. Most immunoglobulin family receptors are homo- or heterodimers that can become activated through ligand interactions. Crosslinking experiments revealed multiple potential higher-order complexes (150, 240, and 300 kDa), suggesting at least one partner of 90 kDa that interact with Toso. We suspect that Toso forms a heterodimer with this other surface protein to collaborate in initiating the anti-apoptotic signal that leads to cFLIP induction. Interactions of surface-expressed Toso complexes with ligands on or near target cells might also modulate the ability of Toso to provide anti-apoptotic signaling. We are currently investigating the existence of such ligands and contributory molecules.

A model summarizing the results is shown in FIG. 10. In this model, stimulation through of the T cell receptor complex transmits activation signals leading to upregulation of Fas and FasL. Activation also induces Toso expression, providing the potential for anti-apoptotic signals that protect against Fas-mediated apoptosis. Toso accomplishes this by forming homo- or heterodimers at the cell surface to generate signals that inhibit the initiation or propagation of caspase-8 activation by cFLIP. It is also possible that Toso requires an extracellular ligand that might modulate its activities. The signaling pathway activated by Toso is clearly important as it leads to induced expression of cFLIP (Irmler, et al. (1997); Srinivasula, et al. (1997)).

EXAMPLE 4

T Cell Signaling Leading to Apoptosis is Blocked by Activated Toso.

Poly (A)'RNA was prepared from Jurkat cells or Jurkat cells stimulated for 24 hours with 10 ng/ml of phorbol 12-myristate 13-acetate (PMA; SIGMA Chemical Company, MO 63178, U.S.A.) and 1 μg/ml phytohemagglutinin (PHA, SIGMA) or 10 ng/ml PMA and 500 ng/ml lonomycin (SIGMA) Poly (A)'RNA (5 μg) was subjected to electrophoresis through 1% agarose gel containing 2.2 M formaldehyde, and transferred to Hybond N' membrane (Amersham Life Science Inc., Inc., 60005, U.S.A.). Hybridization was carried out according to the manufacturer's recommendation. A specific probe for the Toso coding region (1.2 kbp) was synthesized with PCR from pBabeMN-Toso using 5 AGG GGC TCT TGG ATG GAC (TosoS; SEQ ID NO:34) and 5'-CTG GGG TTG ATA GC (TosoA; SEQ ID NO:35). As a control probe, the human β-actin cDNA control probe (CLONTECH Laboratories, Inc., CA 94303–4230) was used. Probes were labeled with $^{32}p$ using a random-primed labeling kit, Prime-a-Gene (Promega). Human RNA Master Blot and Human Immune System Multiple Tissue Northern Blot II (CLONTECH Laboratories) were used to survey Toso mRNA expression in several human tissues. Toso expression was observed in lymph nodes, lung and kidney In addition to these tissues, we detected faint signals from spleen, thymus, liver, heart and salivary gland. Tissues which were analyzed for Toso mRNA include: A1: Whole brain, A2: Amygdala, A3: Caudate nucleus, A4: Cerebellum, A5: Cerebral cortex, A6: Frontal lobe, A7: Hippocampus, A8: Medulla oblongata, B1: Occipital lobe, B2: Putamen, B3: Substantia nigra, B4: Temporal lobe, B5: Thalamus, B6: Subthalamic nucleus, B7: Spinal cord, C1: Heart, C2: Aorta, C3: Skeletal muscle, C4: Colon, C5: Bladder, C6: Uterus, C7: Prostate, C8: Stomach, D1: Testis, D2: Ovary, D3: Pancreas, D4: Pituitary gland, D5: Adrenal gland, D6: Thyroid gland, D7: Salivary gland, D8: Mammary gland, E1: Kidney, E2 Liver, E3: Small intestine, E4: Spleen, E5: Thymus, E6: Peripheral leukocyte, E7: Lymph node, E8: Bone marrow, F1: Appendix, F2: Lung, F3: Trachea, F4: Placenta, G1: Fetal brain, G2: Fetal heart, G3: Fetal kidney, G4: Fetal liver, G5: Fetal spleen, G6: Fetal thymus, G7: Fetal lung. (FIG. 7a). Using Human Immune System Multiple Tissue Northern Blot II, and film exposed at −70° C. with an intensifying screen for one day, endogenous Toso mRNA species of 20 (major), 2.8, 3.5 and 4.3 kbp were detected In lymph node and spleen (see FIG. 7b). The nucleotide length of the cDNA was 1.9 kbp, suggesting that the additional bands might either be alternative splice products or incompletely the processed messages. Toso expression was also observed in peripheral blood leukocytes, thymus (FIG. 7b). Expression in bone marrow and fetal liver was much lower than that in lymph node and spleen as seen after overexposure of the blot (data not shown).

The expression of Toso in several human cell lines was analyzed by semi-quantitative RT-PCR involving amplification of the 1.2 kbp-coding region of Toso (FIG. 7c). The first strand of cDNA was synthesized with 10 μg total RNA from several human cell lines and peripheral blood mononuclear cells. PCR was performed for 35 cycles using TosoS and TosoA. After an initial denaturation at 94° C. for 5 minutes, each cycle of amplification consisted of 30 second denaturation at 94° C., followed by a 30 second-annealing at 58° C. and 2 minutes extension at 72° C. After 35 cycles, the final product was extended for 10 minutes at 72° C. PCR products were electrophoresed through 1.0% agarose gel and transferred to Hybond N+membrane. The BamHI-XhoI fragment (510 bp) of the Toso-coding region were labeled with $^{32}$p Hybridization was carried out as described above.

Toso mRNA was detected in lymphoid cell lines such as Jurkat cells (T cell leukemia), CemT4 cells (T cell leukemia), MolT4 cells (T cell leukemia), HB11.19 cells (B cell lymphoma), a kind gift from Dr. Cleary, M. L., Stanford Univ., and Reh cells (acute lymphocytic leukemia; non T; non B, ATCC). HL-60 cells (promyelocytic leukemia, ATCC) displayed a consistently weak signal. In contrast, Toso PCR products were not detected in non-hematopoietic cell lines including HepG2 cells (hepatoblastoma, a kind gift from Dr. Blau, Stanford Univ.), 293 cells (kidney; transformed with adenovirus, ATCC) and Hela cells (cervix; adenocarcinoma, ATCC). Toso therefore is constitutively expressed in cells of hematopoietic cells.

Toso was expressed in several human cell lines including Jurkat cells, CemT4 cells (human T cell leukemia), SupT1 cells (human T cell leukemia, a kind gift from Dr. Cleary, M. L., Stanford Univ.), Oli-Ly8 cells (human B cell line; transformed with EBV), AMK cells (human B cell line; transformed with EBV), both a gift from Dr. Negrin, R. S., Stanford Univ., Reh cells (acute lymphocytic leukemia; non T; non B), HL-60 cells (promyelocytic leukemia) and HepG2 cells (hepatoma) using pBabeMN-Toso IRES neo to allow cotranslational selection with Geneticin (GIBCO BRL). All of the human T cell lines and one of the human B cell lines, Ocl-Ly8 cells, in which Toso was overexpressed, were inhibited for apoptosis induced by anti-Fas mAb, whereas no significant protection was observed against Fas-induced apoptosis in the other cell lines (data not shown). Thus, the anti-apoptotic effect of Toso also is limited to certain classes of hematopoietic cells, suggesting the presence of tissue-specific mediators in these cells.

T cell activation results in increased expression of Fas and FasL on the cell surface. This is paradoxical, as it is clear that T cells do not kill themselves after such induction, whereas overexpression of Fas and FasL in other cell types does lead to cell death. In vitro, PMA and Ionomycin can induce apoptosis in T cells (Oyalzu, et al., *Biochem. Biophys. Res. Commun.*, 213:994–1001 (1995)) by mimicking certain aspects of CD3 engagement, including upregulation of Fas and FasL. One function of Toso might be to inhibit T cell activated self-killing and that the levels of Toso might become increased following T cell activation, helping to render Jurkat cells partially resistant to upregulated Fas and FasL. Expression of Toso mRNA in Jurkat cells was examined by northern hybridization. As shown in FIG. 8a, an endogenous Toso mRNA species of 2.8 kbp was detected in resting Jurkat cells, although expression was seen after overexposure of the blot (data not shown). Toso mRNA expression increased, including minor species (2.0, 3.5, 4.3, 5.5 kbp), after stimulation of Jurkat cells with PMA and PHA (15-fold increase) or PMA in combination with lonomycin (25-fold increase). Thus, Toso can be induced following T-cell activation. We hypothesize that induced Toso expression would correlate with resistance to Fas-mediated apoptosis.

Jurkat.ecoR cells, Jurkat.ecoR cells infected with pBabeMN-lacZ, and pBabeMN-Toso-infected clones were precultured with 10 ng/ml PMA and 500 ng/ml lonomycin for 12 hours and then incubated with 10 ng/ml of anti-Fas mAb for 24 hours, and as shown in FIG. 8b, Jurkat cells were susceptible to anti-Fas mAb-induced apoptosis as well as PMA/lonomycin-induced apoptosis. However, following activation with PMA/lonomycin one third of Jurkat cells were clearly resistant to anti-Fas mAb induced apoptosis. These results suggest that Jurkat cells activate a protective system that blocks Fas-mediated apoptosis, supporting the contention that induced Toso is a mediator in this protective effect.

We further tested whether Toso expression could rescue activation-induced programmed cell death. We randomly picked five pBabeMN-Toso-infected Fas resistant Jurkat T cell clones and used these to assay the inhibitory effect of Toso on PMA/lonomycin-induced apoptosis. All five clones exhibited significant resistance to PMA/lonomycin-induced apoptosis, as well as continued strong resistance to Fas-induced apoptosis (FIG. 8c). Control clones displayed the expected killing effect when activated with PMA and Ionomycin. Toso not only inhibited apoptosis activated by Fas and TNF-α, but also inhibited apoptosis induced by certain classes of T cell activation events.

Normal T cells at early stages of activation are resistant to Fas-induced apoptosis but become Fas sensitive at late stages of activation (Klas, et al., (1993)). Toso expression kinetics in peripheral blood mononuclear cells were examined after PHA stimulation using by semi-quantitative RT-PCR. Peripheral blood leucocyte (PBL) from healthy volunteers were isolated by Histopaque-1077 (Sigma) density centrifugation. Adherent cells were removed by adherence to plastic culture vessels. Cells were activated with phytohemagglutinin (PHA)-P (1 µg/ml) for 24 hours washed, and cultured with 20 U/ml of recombinant human IL-2 (R&D Systems Inc., Minneapolis, Minn. 55413, U.S.A.). Cells were cultured for one to seven days (day 1, 3, 5, and 7). Toso expression was observed at day 1 and upregulated expression at day 3 after activation. However, Toso expression was clearly decreased at days 5 (FIG. 9a), correlating with Fas sensitivity studies (Klas, et al. (1993)). To perform mixed lymphocyte culture, PBL were treated with 20 µg/ml of mitomycin-C (stimulating cells, SC) for 3 hours and washed. SC were adjusted to $7\times10^5$ cells/ml and cultured with an equal volume and cell density of PBL (responding cells, RC) from another donor (Clot, et al., *Immunology*, 29:445–453 (1975)). Further, allogenic stimulation in mixed lymphocyte cultures was performed to determine whether Toso is activated in primary immune cells upon T cell activation. As shown in FIG. 9b, Toso expression was also rapidly induced in the presence of stimulator cells on day 1; however Toso expression in mixed lymphocyte cultures was reduced by day 6 to levels even lower than seen on day 1 and responder cells alone at day 6. These results further confirm a supportive role for Toso induced resistance to Fas-mediated death during T lymphocyte activation.

Natural T cell resistance to Fas-induced apoptosis shows a time-dependent kinetics (Klas, et al. (1993)). By day 6 post-activation, T cells become susceptible to Fas-induced death. In addition, activation of Jurkat cells by PMA/lonomycin induces a significant increase in Fas ligand expression which is thought to promote apoptosis (Oyalzu, et al. (1995); Brunner, et al., *Nature*, 373:441–444 (1995)). However, PMA/lonomycin-activated Jurkat cells were not as efficiently induced to undergo apoptosis by anti-Fas mAb treatment compared to unstimulated Jurkat cells (FIG. 8b). This suggested that Jurkat cells become at least partly resistant to anti-F as mAb-induced apoptosis after T cell signaling, mimicking processes observed in natural T cells. mRNA expression of Toso in Jurkat cells, as well as in peripheral T cells, is strongly upregulated upon stimulation with T cell activators. Further, overexpression of Toso protected Jurkat cells against PMA/lonomycin—induced apoptosis.

This is consistent with the proposal that Toso expression, which transiently increased and then decreased in peripheral blood mononuclear cells after activation with PHA or allogenic stimulation, is responsible for the temporary Fas resistance in T cells. Hence, the results are consistent with the hypothesis that Toso may be involved in activation-induced resistance to apoptosis of T cells during an immune response. We conclude from the results that the inhibitory effect of the extracellular domain of Toso in activation-induced apoptosis is attributable to the inhibition of Fas-mediated signal transduction through inhibition of caspase-8 by c-FLIP induction.

The finding that Toso can exert cell-specific and signaling pathway specific effects on apoptosis suggests that other polypeptides exist that act upon the Fas death induction cascade. Critically, the fact that signalling by the extracellular domain of Toso induces expression of cFLIP suggests the existence of a regulatable transcription cascade that can be activated to block Fas-mediated apoptosis in some cell types. As shown here, high efficiency gene transduction using a retroviral approach, like other cDNA cloning approaches (Vito, et al., *Science*, 271:521–525 (1996); Kitamura, et al., *Prac. Natl. Acad. Sci* 92:9146–9150 (1995)), allows functional cloning of genes with high throughput and accuracy. Further analysis of the Toso pathway coupled with gene disruption analysis in animals will further clarify the overall role that the extracellular domain of Toso plays in modulating activation-induced T-cell apoptosis in vivo.

EXAMPLE 5
The Cytoplasmic Domain of Toso Promotes Cell Death in Murine preB Cells.

70Z/3 cells were incubated with virus at 32° C. for 12 hours including initial spinning and achieved 70–80% infection efficiency estimated using FACS analysis for pBabeMN-Lyt-2α. 70 Z/3 cells kept about 80% viability at the end of 12 hours incubation with virus. However, after infection, we observed rapid cell death (about 70% of cells were dead) in 70Z/3 cells infected with pBabeMN-Toso, not in 70 Z3 cells with pBabeMN-Lyt-2α nor with supernatant of φNX-E cells (FIG. 11). Supernatant from pBabeMN-Toso transfected 293T cells, which is the parental cell line of φNX-E and φNX-A cells, did not induce rapid cell death to 70Z/3 cells. These results suggest that gene products of Toso induced rapid cell death. Most dead cells after infection showed apoptotic nuclei under microscopic observation, suggesting Toso induced apoptosis to 70Z/3 cells.

To clarify which region was responsible for apoptotic signal transduction, a set of deletion mutants of the Toso cDNA was prepared as shown in Example 3. The mutated Toso cDNA was ligated into pBabeMN retroviral vector and infected 70Z/3 cells. As shown in Table A, below, massive cell death was observed in 70Z/3 cells infected with pBabeMN-Toso.HA, -TosoΔ(377–390).HA, -TosoΔ(334–390).HA and Lyt-2/Toso(271–390).HA, but not pBabeMN-TosoΔ(252–390).HA and pBabeMN-TosoΔ(29–187).HA. Full length Lyt-2 did not induce rapid cell death to 70Z/3 cells after infection (data not shown). Lyt-2/Toso(271–390).HA. was most effective in promoting cell death in 70Z/3 cells, suggesting that the cytoplasmic region was responsible for massive cell death in 70 Z3 cells.

The Toso-induced cell death in 70Z/3 cells, suggests that Toso works not only for protection against Fas-induced apoptosis but also for promotion of cell death. The cytoplasmic domain from $A^{281}$ to $A^{333}$ is responsible for promotion of cell death. BLAST search reveals that this region has partial homology to FAST kinase and acid sphingomyelinase which is involved in Fas-induced apoptosis. When the cytoplasmic domain of Toso is compared to the "death domain" from several molecules, the cytoplasmic domain of Toso did not show any homology to known "death domain", including the consensus sequence as described. The promotion of cell death by Toso was not observed in several cell lines. Cell death induced by Toso may be observed in some stages of B cell development.

Table A indicates the effect of Toso deletion mutants on promotion of apoptosis. 70Z/3 cells were infected with pBabeMN-Lyt-2α.HA, pBabeMN-Toso.HA, pBabeMN-TosoΔ(377–390).HA, pBabeMN-TosoΔ(334–390).HA, pBabeMN-TosoΔ(281–390).HA, pBabeMN-TosoΔ(252–390).HA and pBabeMN-TosoΔ(29–187).HA. After infection, the is stained cells were incubated with phosphate-buffered saline including 100 μg/ml of ethidium bromide (SIGMA) and 100 μg/ml of acridine orange (SIGMA). Viable cells were identified with UV microscopy. The percentage of viable cells is expressed as mean±SD of triplicate cultures.

| Infected-Virus Encoding | % Viable Cells |
| --- | --- |
| Lyt-2.HA | 73 ± 5 |
| 4.8.HA | 30 ± 4 |
| 4.8Δ(377–390).HA | 31 ± 5 |
| 4.8Δ(334–390).HA | 29 ± 2 |
| 4.8Δ(281–390).HA | 75 ± 2 |
| 4.8Δ(252–390).HA | 78 ± 3 |
| 4.8Δ(29–187).HA | 83 ± 3 |
| Lyt-2/4.8(271–390).HA | 5 ± 3 |

I claim:

1. A method of modulating apoptosis in a cell in vitro comprising: administering to said cell an exogenous compound that binds to a Toso protein of said cell, wherein said Toso protein is encoded by a nucleic acid that hybridizes under high stringency conditions to the nucleic acid sequence depicted in FIG. 1 (SEQ ID NO: 1) or its full complement, wherein said binding of the compound to the Toso protein modulates apoptosis in said cell.

2. The method according to claim 1, wherein the binding of said exogenous compound to said Toso protein reduces or eliminates the apoptotic activity of said Toso protein.

3. The method according to claim 1, wherein the binding of said exogenous compound to said Toso protein increases the apoptotic activity of said Toso protein.

* * * * *

SEQUENCE LISTING

<160> NUMBER OF SEQ ID NOS: 35

<210> SEQ ID NO 1
<211> LENGTH: 1911
<212> TYPE: DNA
<213> ORGANISM: Homo sapiens

<400> SEQUENCE: 1
aaaggagtaa gcagcgtgtc tccatccccc tctctagggg ctcttggatg gaccttgcac    60

-continued

```
tctagaaggg acaatggact tctggctttg ccactttac ttcctgccag tatcagggc      120
cctgaggatc ctcccagaag taaaggtaga gggggagctg gcggatcag ttaccatcaa     180
atgcccactt cctgaaatgc atgtgaggat atatctgtgc cgggagatgg ctggatctgg    240
aacatgtggt accgtggtat ccaccaccaa cttcatcaag gcagaataca agggccgagt    300
tactctgaag caatacccac gcaagaatct gttcctagtg gaggtaacac agctgacaga    360
aagtgacagc ggagtctatg cctgcggagc gggcatgaac acagaccggg aaagaccca    420
gaaagtcacc ctgaatgtcc acagtgaata cgagccatca tgggaagagc agccaatgcc    480
tgagactcca aaatggtttc atctgcccta tttgttccag atgcctgcat atgccagttc    540
ttccaaattc gtaaccagag ttaccacacc agctcaaagg gcaaggtcc ctccagttca     600
ccactcctcc cccaccaccc aaatcaccca ccgccctcga gtgtccagag catcttcagt    660
agcaggtgac aagccccgaa ccttcctgcc atccactaca gcctcaaaaa tctcagctct    720
ggagggctg ctcaagcccc agacgcccag ctacaaccac cacaccaggc tgcacaggca    780
gagagcactg gactatggct cacagtctgg gagggaaggc caaggatttc acatcctgat    840
cccgaccatc ctgggccttt tcctgctggc acttctgggg ctggtggtga aagggccgt    900
tgaaaggagg aaagccctct ccaggcgggc ccgccgactg gccgtgagga tgcgcgccct    960
ggagagctcc cagaggcccc gcgggtcgcc gcgaccgcgc tcccaaaaca acatctacag   1020
cgcctgcccg cggcgcgctc gtggagcgga cgctgcaggc acaggggagg ccccgttcc   1080
cggcccccgga gcgccgttgc ccccgcccc gctgcaggtg tctgaatctc cctggctcca   1140
tgccccatct ctgaagacca gctgtgaata cgtgagcctc taccaccagc ctgccgccat   1200
gatggaggac agtgattcag atgactacat caatgttcct gcctgacaac tccccagcta   1260
tccccaacc ccaggctcgg actgtggtgc aaggagtct catctatctg ctgatgtcca    1320
ataccgctt catgtgttct cagagccctc atcacttccc atgccccatc tcgactccca    1380
tccccatcta tctgtggccc tgagcatggc tctgccccca ggtcgtcttg cacaccttgg   1440
cagcccctg tagttgacag gtaagctgta ggcatgtaga gcaattgtcc caatgccact    1500
tgcttccttt ccaagccgtc gaacagactg tgggatttgc agagtgtttc ttccatgtct   1560
ttgaccacag ggtgttgttg ctgccaggct ctagatcaca tggcatcagg ctggggcaga    1620
ggcatagcta ttgtctcggg catccttccc agggttgggt cttacacaaa tagaaggctc    1680
ttgctctgag ttatgtgacg tgcctcagcc ccatggacta agcagggtc tggtataaac    1740
actcctggaa acgcctttgc cctgatccaa atgttagcac ttgctagtga acgtctactt    1800
atctcaagtt ctatgctaaa ggcaatttat cttgatgtga tgataaacca aacttattag    1860
caagatatgc atatatatcc ataaattctc tttactctgt ctccatcctt t             1911
```

<210> SEQ ID NO 2
<211> LENGTH: 390
<212> TYPE: PRT
<213> ORGANISM: Homo sapiens

<400> SEQUENCE: 2

Met Asp Arg Trp Leu Trp Pro Leu Tyr Phe Leu Pro Val Ser Gly Ala
1               5                   10                  15

Leu Arg Ile Leu Pro Glu Val Lys Val Glu Gly Glu Leu Gly Gly Ser
            20                  25                  30

Val Thr Ile Lys Cys Pro Leu Pro Glu Met His Val Arg Ile Tyr Leu
        35                  40                  45

-continued

```
Cys Arg Glu Met Ala Gly Ser Gly Thr Cys Gly Thr Val Val Ser Thr
 50                  55                  60
Thr Asn Phe Ile Lys Ala Glu Tyr Lys Gly Arg Val Thr Leu Lys Gln
 65                  70                  75                  80
Tyr Pro Arg Lys Asn Leu Phe Leu Val Glu Val Thr Gln Leu Thr Glu
                 85                  90                  95
Ser Asp Ser Gly Val Tyr Ala Cys Gly Ala Gly Met Asn Thr Asp Arg
            100                 105                 110
Gly Lys Thr Gln Lys Val Thr Leu Asn Val His Ser Glu Tyr Glu Pro
        115                 120                 125
Ser Trp Glu Gln Pro Met Pro Glu Thr Pro Lys Trp Phe His Leu
    130                 135                 140
Pro Tyr Leu Phe Gln Met Pro Ala Tyr Ala Ser Ser Lys Phe Val
145                 150                 155                 160
Thr Arg Val Thr Thr Pro Ala Gln Arg Gly Lys Val Pro Pro Val His
                165                 170                 175
His Ser Ser Pro Thr Thr Gln Ile Thr His Arg Pro Arg Val Ser Arg
            180                 185                 190
Ala Ser Ser Val Ala Gly Asp Lys Pro Arg Thr Phe Leu Pro Ser Thr
        195                 200                 205
Thr Ala Ser Lys Ile Ser Ala Leu Glu Gly Leu Leu Lys Pro Gln Thr
    210                 215                 220
Pro Ser Tyr Asn His His Thr Arg Leu His Arg Gln Arg Ala Leu Asp
225                 230                 235                 240
Tyr Gly Ser Gln Ser Gly Arg Glu Gly Gln Gly Phe His Ile Leu Ile
                245                 250                 255
Pro Thr Ile Leu Gly Leu Phe Leu Leu Ala Leu Leu Gly Leu Val Val
            260                 265                 270
Lys Arg Ala Val Glu Arg Arg Lys Ala Leu Ser Arg Arg Ala Arg Arg
        275                 280                 285
Leu Ala Val Arg Met Arg Ala Leu Glu Ser Ser Gln Arg Pro Arg Gly
    290                 295                 300
Ser Pro Arg Pro Arg Ser Gln Asn Asn Ile Tyr Ser Ala Cys Pro Arg
305                 310                 315                 320
Arg Ala Arg Gly Ala Asp Ala Ala Gly Thr Gly Glu Ala Pro Val Pro
                325                 330                 335
Gly Pro Gly Ala Pro Leu Pro Pro Ala Pro Leu Gln Val Ser Glu Ser
            340                 345                 350
Pro Trp Leu His Ala Pro Ser Leu Lys Thr Ser Cys Glu Tyr Val Ser
    355                 360                 365
Leu Tyr His Gln Pro Ala Ala Met Met Glu Asp Ser Asp Ser Asp Asp
    370                 375                 380
Tyr Ile Asn Val Pro Ala
385                 390

<210> SEQ ID NO 3
<211> LENGTH: 73
<212> TYPE: PRT
<213> ORGANISM: Homo sapiens

<400> SEQUENCE: 3

Val Thr Ile Lys Cys Pro Leu Pro Glu Met His Val Arg Ile Tyr Leu
 1               5                  10                  15
Cys Arg Glu Met Ala Gly Ser Gly Thr Cys Gly Thr Val Val Ser Thr
```

-continued

```
                    20                  25                  30
Thr Asn Phe Ile Lys Ala Glu Trp Lys Gly Arg Val Thr Leu Lys Gln
            35                  40                  45
Tyr Pro Arg Lys Asn Leu Phe Leu Val Glu Val Thr Gln Leu Thr Glu
        50                  55                  60
Ser Asp Ser Gly Val Tyr Ala Cys Gly
65                  70

<210> SEQ ID NO 4
<211> LENGTH: 79
<212> TYPE: PRT
<213> ORGANISM: Homo sapiens

<400> SEQUENCE: 4

Leu Ser Leu Thr Cys Thr Val Ser Gly Ser Thr Phe Ser Asn Asp Tyr
1               5                   10                  15
Tyr Thr Trp Val Arg Gln Pro Pro Gly Arg Gly Leu Glu Trp Ile Gly
                20                  25                  30
Tyr Val Phe Tyr His Gly Thr Ser Asp Asp Thr Thr Pro Leu Arg Ser
            35                  40                  45
Arg Val Thr Met Leu Val Asp Thr Ser Lys Asn Gln Phe Ser Leu Arg
        50                  55                  60
Leu Ser Ser Val Thr Ala Ala Asp Thr Ala Val Tyr Tyr Cys Ala
65                  70                  75

<210> SEQ ID NO 5
<211> LENGTH: 73
<212> TYPE: PRT
<213> ORGANISM: Homo sapiens

<400> SEQUENCE: 5

Val Thr Leu Thr Cys Arg Ser Ser Thr Gly Ala Val Thr Thr Ser Asn
1               5                   10                  15
Tyr Ala Asn Trp Val Gln Gln Lys Pro Asp His Leu Phe Thr Gly Ile
                20                  25                  30
Gly Gly Thr Asn Asn Arg Ala Pro Gly Val Pro Ala Arg Phe Ser Gly
            35                  40                  45
Ser Leu Ile Gly Asn Lys Ala Ala Leu Thr Ile Thr Gly Ala Gln Thr
        50                  55                  60
Glu Asp Glu Ala Ile Tyr Phe Cys Ala
65                  70

<210> SEQ ID NO 6
<211> LENGTH: 72
<212> TYPE: PRT
<213> ORGANISM: Homo sapiens

<400> SEQUENCE: 6

Thr Ser Leu Asn Cys Thr Phe Ser Asp Ser Ala Ser Gln Tyr Phe Trp
1               5                   10                  15
Trp Tyr Arg Gln His Ser Gly Lys Ala Pro Lys Ala Leu Met Ser Ile
                20                  25                  30
Phe Ser Asn Gly Glu Lys Glu Glu Gly Arg Phe Thr Ile His Leu Asn
            35                  40                  45
Lys Ala Ser Leu His Phe Ser Leu His Ile Arg Asp Ser Gln Pro Ser
        50                  55                  60
Asp Ser Ala Leu Tyr Leu Cys Ala
65                  70
```

<210> SEQ ID NO 7
<211> LENGTH: 75
<212> TYPE: PRT
<213> ORGANISM: Homo sapiens

<400> SEQUENCE: 7

```
Val Thr Leu Arg Cys Lys Pro Ile Ser Gly His Asn Ser Leu Phe Trp
 1               5                  10                  15
Tyr Arg Gln Thr Met Met Arg Gly Leu Glu Leu Leu Ile Tyr Phe Asn
                20                  25                  30
Asn Asn Val Pro Ile Asp Asp Ser Gly Met Pro Glu Asp Arg Phe Ser
            35                  40                  45
Ala Lys Met Pro Asn Ala Ser Phe Ser Thr Leu Lys Ile Gln Pro Ser
        50                  55                  60
Glu Pro Arg Asp Ser Ala Val Tyr Phe Cys Ala
 65                  70                  75
```

<210> SEQ ID NO 8
<211> LENGTH: 74
<212> TYPE: PRT
<213> ORGANISM: Homo sapiens

<400> SEQUENCE: 8

```
Val Glu Leu Thr Cys Thr Ala Ser Gln Lys Lys Ser Ile Gln Phe His
 1               5                  10                  15
Trp Lys Asn Ser Asn Gln Ile Lys Ile Leu Gly Asn Gln Gly Ser Phe
                20                  25                  30
Leu Thr Lys Gly Pro Ser Lys Leu Asn Asp Arg Ala Asp Ser Arg Arg
            35                  40                  45
Ser Leu Trp Asp Gln Gly Asn Phe Pro Leu Ile Ile Lys Asn Leu Lys
        50                  55                  60
Ile Glu Asp Ser Asp Thr Tyr Ile Cys Glu
 65                  70
```

<210> SEQ ID NO 9
<211> LENGTH: 80
<212> TYPE: PRT
<213> ORGANISM: Homo sapiens

<400> SEQUENCE: 9

```
Ala Lys Met Ser Cys Glu Ala Lys Thr Phe Pro Lys Gly Thr Thr Ile
 1               5                  10                  15
Tyr Trp Leu Arg Glu Leu Gln Asp Ser Asn Lys Asn Lys His Phe Glu
                20                  25                  30
Phe Leu Ala Ser Arg Thr Ser Thr Lys Gly Ile Lys Tyr Gly Glu Arg
            35                  40                  45
Val Lys Lys Asn Met Thr Leu Ser Phe Asn Ser Thr Leu Pro Phe Leu
        50                  55                  60
Lys Ile Met Asp Val Lys Pro Glu Asp Ser Gly Phe Tyr Phe Cys Ala
 65                  70                  75                  80
```

<210> SEQ ID NO 10
<211> LENGTH: 76
<212> TYPE: PRT
<213> ORGANISM: Homo sapiens

<400> SEQUENCE: 10

```
Val Thr Ile Thr Cys Pro Phe Thr Tyr Ala Thr Arg Gln Leu Lys Lys
```

```
              1               5                  10                 15
Ser Phe Tyr Lys Val Glu Asp Gly Glu Leu Val Leu Ile Ile Asp Ser
                 20                 25                 30

Ser Ser Lys Glu Ala Lys Asp Pro Arg Tyr Lys Gly Arg Ile Thr Leu
                 35                 40                 45

Gln Ile Gln Ser Thr Thr Ala Lys Glu Phe Thr Val Thr Leu Lys His
                 50                 55                 60

Leu Gln Leu Asn Asp Ala Gly Gln Tyr Val Cys Gln
 65                 70                 75
```

<210> SEQ ID NO 11
<211> LENGTH: 84
<212> TYPE: PRT
<213> ORGANISM: Homo sapiens
<220> FEATURE:
<221> NAME/KEY: MISC_FEATURE
<222> LOCATION: (6)..(51)
<223> OTHER INFORMATION: "Xaa" at positions 6-7, 9-18, 20, 22, 25-32,
      34-35, 37-48 and 50-51 can be any amino acid.
<220> FEATURE:
<221> NAME/KEY: MISC_FEATURE
<222> LOCATION: (53)..(53)
<223> OTHER INFORMATION: "Xaa" at position 53 can be Phe, Val, or Ile.
<220> FEATURE:
<221> NAME/KEY: MISC_FEATURE
<222> LOCATION: (54)..(76)
<223> OTHER INFORMATION: "Xaa" at positions 54-65, 71, and 73-76 can be
      any amino acid.
<220> FEATURE:
<221> NAME/KEY: MISC_FEATURE
<222> LOCATION: (79)..(79)
<223> OTHER INFORMATION: "Xaa" at position 79 can be either Ala or Gly.
<220> FEATURE:
<221> NAME/KEY: MISC_FEATURE
<222> LOCATION: (80)..(82)
<223> OTHER INFORMATION: "Xaa" at positions 80 and 82 can be any amino
      acid.

<400> SEQUENCE: 11

```
Val Thr Leu Thr Cys Xaa Xaa Ser Xaa Xaa Xaa Xaa Xaa Xaa Xaa Xaa
 1               5                  10                 15

Xaa Xaa Phe Xaa Trp Xaa Arg Gln Xaa Xaa Xaa Xaa Xaa Xaa Xaa Xaa
                 20                 25                 30

Leu Xaa Xaa Tyr Xaa Xaa Xaa Xaa Xaa Xaa Xaa Xaa Xaa Xaa Xaa Xaa
                 35                 40                 45

Tyr Xaa Xaa Arg Xaa Xaa Xaa Xaa Xaa Xaa Xaa Xaa Xaa Xaa Xaa Xaa
             50                 55                 60

Xaa Phe Ser Leu Thr Ile Xaa Asn Xaa Xaa Xaa Xaa Asp Ser Xaa Xaa
 65                 70                 75                 80

Tyr Xaa Cys Ala
```

<210> SEQ ID NO 12
<211> LENGTH: 43
<212> TYPE: PRT
<213> ORGANISM: Homo sapiens

<400> SEQUENCE: 12

```
Gln Arg Pro Arg Gly Ser Pro Arg Pro Arg Ser Gln Asn Asn Ile Tyr
 1               5                  10                 15

Ser Ala Cys Pro Arg Arg Ala Arg Gly Ala Asp Ala Ala Gly Thr Gly
                 20                 25                 30

Glu Ala Pro Val Pro Gly Pro Gly Ala Pro Leu
                 35                 40
```

```
<210> SEQ ID NO 13
<211> LENGTH: 35
<212> TYPE: PRT
<213> ORGANISM: Homo sapiens

<400> SEQUENCE: 13

Arg Arg Pro Arg Gly Glu Pro Gly Pro Arg Ala Pro Arg Pro Thr Glu
1               5                   10                  15

Gly Ala Thr Cys Ala Gly Pro Gly Glu Ser Trp Ser Pro Ser Pro Asn
                20                  25                  30

Ser Met Leu
        35

<210> SEQ ID NO 14
<211> LENGTH: 36
<212> TYPE: PRT
<213> ORGANISM: Homo sapiens

<400> SEQUENCE: 14

Met Pro Pro Arg Tyr Gly Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
                20                  25                  30

Met Gly Leu Val
        35

<210> SEQ ID NO 15
<211> LENGTH: 19
<212> TYPE: PRT
<213> ORGANISM: Homo sapiens

<400> SEQUENCE: 15

Glu Ser Pro Trp Leu His Ala Pro Ser Leu Lys Thr Ser Cys Glu Tyr
1               5                   10                  15

Val Ser Leu

<210> SEQ ID NO 16
<211> LENGTH: 19
<212> TYPE: PRT
<213> ORGANISM: Homo sapiens

<400> SEQUENCE: 16

Asp Ala Pro Trp Gln Gln His Ala Arg Trp Tyr Asp Arg Cys Glu Tyr
1               5                   10                  15

Val Leu Leu

<210> SEQ ID NO 17
<211> LENGTH: 19
<212> TYPE: PRT
<213> ORGANISM: Homo sapiens

<400> SEQUENCE: 17

Gln Gln Pro Leu Leu His Pro Pro Glu Pro Lys Ser Pro Gly Glu Tyr
1               5                   10                  15

Val Asn Ile

<210> SEQ ID NO 18
<211> LENGTH: 19
<212> TYPE: PRT
<213> ORGANISM: Homo sapiens
```

-continued

<400> SEQUENCE: 18

Trp Glu Pro Trp Leu Pro Ala Glu Ala Leu Thr Arg Leu Arg Ile Gly
1               5                   10                  15

Gly Phe Tyr

<210> SEQ ID NO 19
<211> LENGTH: 19
<212> TYPE: PRT
<213> ORGANISM: Homo sapiens

<400> SEQUENCE: 19

Gln Pro Ala Ala Met Met Glu Asp Ser Asp Ser Asp Asp Tyr Ile Asn
1               5                   10                  15

Val Pro Ala

<210> SEQ ID NO 20
<211> LENGTH: 19
<212> TYPE: PRT
<213> ORGANISM: Homo sapiens

<400> SEQUENCE: 20

Thr Glu Ala Cys Val Val Arg Asp Ala Asp Asn Glu Pro His Ile Glu
1               5                   10                  15

Arg Pro Ala

<210> SEQ ID NO 21
<211> LENGTH: 19
<212> TYPE: PRT
<213> ORGANISM: Homo sapiens

<400> SEQUENCE: 21

Gln Pro Ala Pro Arg Glu Glu Thr Gly Thr Glu Glu Tyr Met Lys
1               5                   10                  15

Met Asp Leu

<210> SEQ ID NO 22
<211> LENGTH: 20
<212> TYPE: DNA
<213> ORGANISM: Artificial sequence
<220> FEATURE:
<223> OTHER INFORMATION: synthetic

<400> SEQUENCE: 22
gctcacttac aggctctcta                                           20

<210> SEQ ID NO 23
<211> LENGTH: 20
<212> TYPE: DNA
<213> ORGANISM: Artificial sequence
<220> FEATURE:
<223> OTHER INFORMATION: synthetic

<400> SEQUENCE: 23
caggtggggt ctttcattcc                                           20

<210> SEQ ID NO 24
<211> LENGTH: 5
<212> TYPE: PRT
<213> ORGANISM: Homo sapiens

<400> SEQUENCE: 24

Val Thr Leu Thr Cys

<210> SEQ ID NO 25
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: "Xaa" at position 3 can be Gly or Ala.
<220> FEATURE:
<221> NAME/KEY: MISC_FEATURE
<222> LOCATION: (4)..(6)
<223> OTHER INFORMATION: "Xaa" at positions 4 and 6 can be any amino acid.

<400> SEQUENCE: 25

Asp Ser Xaa Xaa Tyr Xaa Cys Ala
1               5

<210> SEQ ID NO 26
<211> LENGTH: 5
<212> TYPE: PRT
<213> ORGANISM: Homo sapiens

<400> SEQUENCE: 26

Val Thr Ile Lys Cys
1               5

<210> SEQ ID NO 27
<211> LENGTH: 7
<212> TYPE: PRT
<213> ORGANISM: Homo sapiens

<400> SEQUENCE: 27

Asp Ser Gly Val Tyr Ala Cys
1               5

<210> SEQ ID NO 28
<211> LENGTH: 27
<212> TYPE: DNA
<213> ORGANISM: Artificial sequence
<220> FEATURE:
<223> OTHER INFORMATION: primer

<400> SEQUENCE: 28
agaattctct ctaggggctc ttggatg                              27

<210> SEQ ID NO 29
<211> LENGTH: 29
<212> TYPE: DNA
<213> ORGANISM: Artificial sequence
<220> FEATURE:
<223> OTHER INFORMATION: primer

<400> SEQUENCE: 29
ataaagcttc tcagggcaca gatagatgg                            29

<210> SEQ ID NO 30
<211> LENGTH: 22
<212> TYPE: DNA
<213> ORGANISM: Artificial sequence
<220> FEATURE:
<223> OTHER INFORMATION: primer

<400> SEQUENCE: 30
agaggcatag ctattgtctc gg                                   22

```
<210> SEQ ID NO 31
<211> LENGTH: 20
<212> TYPE: DNA
<213> ORGANISM: Artificial sequence
<220> FEATURE:
<223> OTHER INFORMATION: primer

<400> SEQUENCE: 31
acatttggat cagggcaaag                                                    20

<210> SEQ ID NO 32
<211> LENGTH: 20
<212> TYPE: DNA
<213> ORGANISM: Artificial sequence
<220> FEATURE:
<223> OTHER INFORMATION: primer

<400> SEQUENCE: 32
gggagaagta aagaacaaag                                                    20

<210> SEQ ID NO 33
<211> LENGTH: 20
<212> TYPE: DNA
<213> ORGANISM: Artificial sequence
<220> FEATURE:
<223> OTHER INFORMATION: primer

<400> SEQUENCE: 33
cgtaggcaca atcacagcat                                                    20

<210> SEQ ID NO 34
<211> LENGTH: 18
<212> TYPE: DNA
<213> ORGANISM: Artificial sequence
<220> FEATURE:
<223> OTHER INFORMATION: primer

<400> SEQUENCE: 34
aggggctctt ggatggac                                                      18

<210> SEQ ID NO 35
<211> LENGTH: 17
<212> TYPE: DNA
<213> ORGANISM: Artificial sequence
<220> FEATURE:
<223> OTHER INFORMATION: primer

<400> SEQUENCE: 35
ctggggttgg ggatagc                                                       17
```